(12) United States Patent
Maenaka et al.

(10) Patent No.: US 10,429,394 B2
(45) Date of Patent: Oct. 1, 2019

(54) MONOCLONAL ANTIBODIES AGAINST KIR2DS1

(71) Applicant: National University Corporation Hokkaido University, Sapporo-shi (JP)

(72) Inventors: Katsumi Maenaka, Sapporo (JP); Kimiko Kuroki, Sapporo (JP); Hiroshi Maita, Sapporo (JP); Hideo Fukuhara, Sapporo (JP)

(73) Assignee: National University Corporation Hokkaido, Hokkaido (JP)

( * ) Notice: Subject to any disclaimer, the term of this patent is extended or adjusted under 35 U.S.C. 154(b) by 0 days.

(21) Appl. No.: 15/507,698

(22) PCT Filed: Aug. 27, 2015

(86) PCT No.: PCT/JP2015/074295
§ 371 (c)(1),
(2) Date: Jul. 14, 2017

(87) PCT Pub. No.: WO2016/031936
PCT Pub. Date: Mar. 3, 2016

(65) Prior Publication Data
US 2017/0350892 A1 Dec. 7, 2017

(30) Foreign Application Priority Data
Aug. 29, 2014 (JP) .................. 2014-176094

(51) Int. Cl.
| | | |
|---|---|---|
| G01N 33/577 | (2006.01) | |
| C07K 16/28 | (2006.01) | |
| C12N 5/10 | (2006.01) | |
| C12N 15/02 | (2006.01) | |
| G01N 33/53 | (2006.01) | |
| A61K 39/395 | (2006.01) | |
| C12N 15/09 | (2006.01) | |
| C07K 16/00 | (2006.01) | |
| C07K 1/00 | (2006.01) | |

(52) U.S. Cl.
CPC ......... *G01N 33/577* (2013.01); *A61K 39/395* (2013.01); *C07K 16/28* (2013.01); *C12N 5/10* (2013.01); *C12N 15/02* (2013.01); *C12N 15/09* (2013.01); *G01N 33/53* (2013.01); *C07K 1/00* (2013.01); *C07K 16/00* (2013.01)

(58) Field of Classification Search
None
See application file for complete search history.

(56) References Cited

U.S. PATENT DOCUMENTS
| | | |
|---|---|---|
| 2006/0263361 A1 | 11/2006 | Morella et al. |
| 2014/0023646 A1 | 1/2014 | Wagtmann et al. |
| 2015/0344576 A1 | 12/2015 | Moretta et al. |

FOREIGN PATENT DOCUMENTS
| | | |
|---|---|---|
| JP | 2007-524612 A | 8/2007 |
| JP | 2008-506368 A | 3/2008 |
| JP | 2008-526812 A | 7/2008 |
| WO | 2007042573 A2 | 4/2007 |

OTHER PUBLICATIONS

Lloyd et al., Protein Engineering, Design & Selection, 22, 159-168, 2009 (Year: 2009).*
Benson Jr., et al., IPH2101, a novel anti-inhibitory KIR antibody, and lenalidomide combine to enhance the natural killer cell versus multiple myeloma effect, Blood, 2011, 118: 6387-6391.
Benson Jr., et al., A phase 1 trial of the anti-KIR antibody IPH2101 in patients with relapsed/refractory multiple myeloma, Blood, 2012, 120: 4324-4333.
David et al., Discrimination between the main activating and inhibitory killer cell immunoglobulin-like receptor positive natural killer cell subsets using newly characterized monoclonal antibodies, Immunology, 2009, 128, 172-184.
Johansson et al., NK cell activation by KIR-binding antibody 1-7F9 and response to HIV-infected autologous cells in viremic and controller HIV-infected patients, Clinical Immunology, 2010, 134, 158-168.
Romagné et al., Preclinical characterization of 1-7F9, a novel human anti-KIR receptor therapeutic antibody that augments natural killer-mediated killing of tumor cells, Blood, 2009, 114: 2667-2677.
Vey, et al., A phase 1 trial of the anti-inhibitory KIR mAb IPH2101 for AML in complete remission, Blood, 2012, 120: 4317-4323.

* cited by examiner

*Primary Examiner* — Elly-Gerald Stoica
(74) *Attorney, Agent, or Firm* — K&L Gates LLP; Louis C. Cullman; David Diamond

(57) ABSTRACT

A monoclonal antibody to KIR2DS1 or a fragment containing an antigen-binding region thereof has VL having an amino acid sequence of SEQ ID NO: 1 or an amino acid sequence having the same amino acid sequence as the amino acid sequence except that one or several amino acids are conservatively substituted as CDR1, having an amino acid sequence of SEQ ID NO: 2 or an amino acid sequence having the same amino acid sequence as the amino acid sequence except that one or several amino acids are conservatively substituted as CDR2, and having an amino acid sequence of SEQ ID NO: 3 or an amino acid sequence having the same amino acid sequence as the amino acid sequence except that one or several amino acids are conservatively substituted as CDR3; and VH having an amino acid sequence of SEQ ID NO: 4 or SEQ ID NO: 5 or an amino acid sequence having the same amino acid sequence as the amino acid sequence except that one or several amino acids are conservatively substituted as CDR1, having an amino acid sequence of SEQ ID NO: 6 or an amino acid sequence having the same amino acid sequence as the amino acid sequence except that one or several amino acids are conservatively substituted as CDR2, and having an amino acid sequence of any one selected from the group consisting of SEQ ID NO: 7, SEQ ID NO: 8, and SEQ ID NO: 9 or an amino acid sequence having the same amino acid sequence as the amino acid sequence except that one or several amino acids are conservatively substituted as CDR3.

14 Claims, 4 Drawing Sheets

Specification includes a Sequence Listing.

(a)

(b)

(c)

(d)

SEQUENCE LISTING

```
<160> NUMBER OF SEQ ID NOS: 95

<210> SEQ ID NO 1
<211> LENGTH: 11
<212> TYPE: PRT
<213> ORGANISM: Artificial
<220> FEATURE:
<223> OTHER INFORMATION: VL CDR1

<400> SEQUENCE: 1

Lys Ala Ser Gln Asn Val Gly Ser Asn Val Asp
1               5                   10

<210> SEQ ID NO 2
<211> LENGTH: 7
<212> TYPE: PRT
<213> ORGANISM: Artificial
<220> FEATURE:
<223> OTHER INFORMATION: VL CDR2

<400> SEQUENCE: 2

Lys Ala Ser Asn Arg Tyr Thr
1               5

<210> SEQ ID NO 3
<211> LENGTH: 9
<212> TYPE: PRT
<213> ORGANISM: Artificial
<220> FEATURE:
<223> OTHER INFORMATION: VL CDR3

<400> SEQUENCE: 3

Met Gln Ser Asn Thr Asn Pro Leu Thr
1               5

<210> SEQ ID NO 4
<211> LENGTH: 12
<212> TYPE: PRT
<213> ORGANISM: Artificial
<220> FEATURE:
<223> OTHER INFORMATION: VH CDR1
```

-continued

```
<400> SEQUENCE: 4

Gly Phe Ser Leu Ser Thr Tyr Ser Met Gly Val Ser
1               5                   10

<210> SEQ ID NO 5
<211> LENGTH: 12
<212> TYPE: PRT
<213> ORGANISM: Artificial
<220> FEATURE:
<223> OTHER INFORMATION: VH CDR1

<400> SEQUENCE: 5

Gly Phe Ser Leu Ser Thr Tyr Gly Met Gly Val Ser
1               5                   10

<210> SEQ ID NO 6
<211> LENGTH: 17
<212> TYPE: PRT
<213> ORGANISM: Artificial
<220> FEATURE:
<223> OTHER INFORMATION: VH CDR2

<400> SEQUENCE: 6

Ala Ser Ile Trp Trp Asn Gly Asn Thr Tyr Asn Asn Pro Ser Leu Lys
1               5                   10                  15

Ser

<210> SEQ ID NO 7
<211> LENGTH: 14
<212> TYPE: PRT
<213> ORGANISM: Artificial
<220> FEATURE:
<223> OTHER INFORMATION: VH CDR3

<400> SEQUENCE: 7

Thr Glu Ile Ile Arg Gly Arg Asn Tyr Tyr Val Met Asp Ala
1               5                   10

<210> SEQ ID NO 8
<211> LENGTH: 14
<212> TYPE: PRT
<213> ORGANISM: Artificial
<220> FEATURE:
<223> OTHER INFORMATION: VH CDR3

<400> SEQUENCE: 8

Thr Leu Ile Thr Ile Thr Pro Phe Tyr Tyr Val Met Asp Ala
1               5                   10

<210> SEQ ID NO 9
<211> LENGTH: 16
<212> TYPE: PRT
<213> ORGANISM: Artificial
<220> FEATURE:
<223> OTHER INFORMATION: VH CDR3

<400> SEQUENCE: 9

Thr Leu Ile Thr Ile Ala Ala Ile Ser His Tyr Tyr Val Met Asp Ala
1               5                   10                  15

<210> SEQ ID NO 10
<211> LENGTH: 33
<212> TYPE: DNA
<213> ORGANISM: Artificial
<220> FEATURE:
<223> OTHER INFORMATION: VL CDR1
```

```
<400> SEQUENCE: 10
aaggccagtc agaatgtggg ttctaatgta gac                          33

<210> SEQ ID NO 11
<211> LENGTH: 21
<212> TYPE: DNA
<213> ORGANISM: Artificial
<220> FEATURE:
<223> OTHER INFORMATION: VL CDR2

<400> SEQUENCE: 11
aaggcatcca accggtacac t                                      21

<210> SEQ ID NO 12
<211> LENGTH: 27
<212> TYPE: DNA
<213> ORGANISM: Artificial
<220> FEATURE:
<223> OTHER INFORMATION: VL CDR3

<400> SEQUENCE: 12
atgcagtcta acaccaatcc gctcacg                                27

<210> SEQ ID NO 13
<211> LENGTH: 36
<212> TYPE: DNA
<213> ORGANISM: Artificial
<220> FEATURE:
<223> OTHER INFORMATION: VH CDR1

<400> SEQUENCE: 13
ggattttcac tgagcactta tagtatgggt gtgagc                      36

<210> SEQ ID NO 14
<211> LENGTH: 36
<212> TYPE: DNA
<213> ORGANISM: Artificial
<220> FEATURE:
<223> OTHER INFORMATION: VH CDR1

<400> SEQUENCE: 14
ggattttcac tgagcactta tggtatgggt gtgagc                      36

<210> SEQ ID NO 15
<211> LENGTH: 51
<212> TYPE: DNA
<213> ORGANISM: Artificial
<220> FEATURE:
<223> OTHER INFORMATION: VH CDR2

<400> SEQUENCE: 15
gcaagcattt ggtggaatgg taatacatac aacaacccat ctctgaagag c      51

<210> SEQ ID NO 16
<211> LENGTH: 42
<212> TYPE: DNA
<213> ORGANISM: Artificial
<220> FEATURE:
<223> OTHER INFORMATION: VH CDR3

<400> SEQUENCE: 16
acggaaataa ttcggggtag gaattactat gttatggatg cc               42
```

-continued

```
<210> SEQ ID NO 17
<211> LENGTH: 42
<212> TYPE: DNA
<213> ORGANISM: Artificial
<220> FEATURE:
<223> OTHER INFORMATION: VH CDR3

<400> SEQUENCE: 17
accctcatta ctataacacc tttttactat gttatggatg cc                           42

<210> SEQ ID NO 18
<211> LENGTH: 48
<212> TYPE: DNA
<213> ORGANISM: Artificial
<220> FEATURE:
<223> OTHER INFORMATION: VH CDR3

<400> SEQUENCE: 18
actcttatta ctatagcagc tatatcccat tactatgtta tggatgcc                     48

<210> SEQ ID NO 19
<211> LENGTH: 609
<212> TYPE: DNA
<213> ORGANISM: Homo sapiens

<400> SEQUENCE: 19
atgcacgagg gagtccacag aaaaccttcc ctcctggccc acccaggtcg cctggtgaaa        60
tcagaagaga cagtcatcct gcaatgttgg tcagatgtca tgtttgaaca cttccttctg       120
cacagagagg ggatgtttaa cgacactttg cgcctcattg agaacaccat gatggggtc        180 tccaaggcca acttctccat cagtcgcatg cggcaagacc tggcagggac ctacagatgc       240
tacggttctg ttactcactc cccctatcag ctgtcagctc ccagtgaccc tctggacatc       300
gtgatcatag gtctatatga aaaccttct ctctcagccc agccgggccc cacggttctg        360
gcaggagaga atgtgacctt gtcctgcagc tcccggagct cctatgacat gtaccatcta       420
tccagggaag gggaggccca tgaacgtagg ctccctgcag ggaccaaggt caacggaaca       480
ttccaggcta actttcctct gggccctgcc acccacggag ggacctacag atgcttcggc       540
tctttccgtg actctccata cgagtggtca aagtcaagtg acccactgct tgtttctgtc       600
acatagtaa                                                               609

<210> SEQ ID NO 20
<211> LENGTH: 201
<212> TYPE: PRT
<213> ORGANISM: Homo sapiens

<400> SEQUENCE: 20

Met His Glu Gly Val His Arg Lys Pro Ser Leu Leu Ala His Pro Gly
1               5                   10                  15

Arg Leu Val Lys Ser Glu Glu Thr Val Ile Leu Gln Cys Trp Ser Asp
            20                  25                  30

Val Met Phe Glu His Phe Leu Leu His Arg Glu Gly Met Phe Asn Asp
        35                  40                  45

Thr Leu Arg Leu Ile Gly Glu His His Asp Gly Val Ser Lys Ala Asn
    50                  55                  60

Phe Ser Ile Ser Arg Met Arg Gln Asp Leu Ala Gly Thr Tyr Arg Cys
65                  70                  75                  80

Tyr Gly Ser Val Thr His Ser Pro Tyr Gln Leu Ser Ala Pro Ser Asp
                85                  90                  95
```

Pro Leu Asp Ile Val Ile Ile Gly Leu Tyr Glu Lys Pro Ser Leu Ser
            100                 105                 110

Ala Gln Pro Gly Pro Thr Val Leu Ala Gly Glu Asn Val Thr Leu Ser
        115                 120                 125

Cys Ser Ser Arg Ser Ser Tyr Asp Met Tyr His Leu Ser Arg Glu Gly
    130                 135                 140

Glu Ala His Glu Arg Arg Leu Pro Ala Gly Thr Lys Val Asn Gly Thr
145                 150                 155                 160

Phe Gln Ala Asn Phe Pro Leu Gly Pro Ala Thr His Gly Gly Thr Tyr
                165                 170                 175

Arg Cys Phe Gly Ser Phe Arg Asp Ser Pro Tyr Glu Trp Ser Lys Ser
            180                 185                 190

Ser Asp Pro Leu Leu Val Ser Val Thr
        195                 200

<210> SEQ ID NO 21
<211> LENGTH: 609
<212> TYPE: DNA
<213> ORGANISM: Homo sapiens

<400> SEQUENCE: 21
atgcacgagg gagtccacag aaaaccttcc ctcctggccc acccaggtcc cctggtgaaa      60
tcagaagaga cagtcatcct gcaatgttgg tcagatgtca tgtttgaaca cttccttctg     120
cacagagagg ggatgtttaa cgacactttg cgcctcattg agaacaccca tgatggggtc     180
tccaaggcca acttctccat cagtcgcatg acgcaagacc tggcagggac ctacagatgc     240
tacggttctg ttactcactc cccctatcag gtgtcagctc ccagtgaccc tctggacatc     300
gtgatcatag tctatatga gaaaccttct ctctcagccc agccgggccc cacggttctg     360
gcaggagaga atgtgacctt gtcctgcagc tcccggagct cctatgacat gtaccatcta     420
tccagggaag gggaggccca tgaacgtagg ctccctgcag ggcccaaggt caacggaaca     480
ttccaggctg actttcctct gggccctgcc acccacggag ggacctacag atgcttcggc     540
tctttccatg actctccata cgagtggtca aagtcaagtg acccactgct tgtttctgtc     600
acatagtaa                                                              609

<210> SEQ ID NO 22
<211> LENGTH: 201
<212> TYPE: PRT
<213> ORGANISM: Homo sapiens

<400> SEQUENCE: 22

Met His Glu Gly Val His Arg Lys Pro Ser Leu Leu Ala His Pro Gly
1               5                   10                  15

Pro Leu Val Lys Ser Glu Glu Thr Val Ile Leu Gln Cys Trp Ser Asp
            20                  25                  30

Val Met Phe Glu His Phe Leu Leu His Arg Glu Gly Met Phe Asn Asp
        35                  40                  45

Thr Leu Arg Leu Ile Gly Glu His His Asp Gly Val Ser Lys Ala Asn
    50                  55                  60

Phe Ser Ile Ser Arg Met Thr Gln Asp Leu Ala Gly Thr Tyr Arg Cys
65                  70                  75                  80

Tyr Gly Ser Val Thr His Ser Pro Tyr Gln Val Ser Ala Pro Ser Asp
                85                  90                  95

Pro Leu Asp Ile Val Ile Ile Gly Leu Tyr Glu Lys Pro Ser Leu Ser
            100                 105                 110

-continued

```
Ala Gln Pro Gly Pro Thr Val Leu Ala Gly Glu Asn Val Thr Leu Ser
            115                 120                 125
Cys Ser Ser Arg Ser Ser Tyr Asp Met Tyr His Leu Ser Arg Glu Gly
130                 135                 140
Glu Ala His Glu Arg Arg Leu Pro Ala Gly Pro Lys Val Asn Gly Thr
145                 150                 155                 160
Phe Gln Ala Asp Phe Pro Leu Gly Pro Ala Thr His Gly Gly Thr Tyr
                165                 170                 175
Arg Cys Phe Gly Ser Phe His Asp Ser Pro Tyr Glu Trp Ser Lys Ser
            180                 185                 190
Ser Asp Pro Leu Leu Val Ser Val Thr
            195                 200
```

<210> SEQ ID NO 23
<211> LENGTH: 17
<212> TYPE: DNA
<213> ORGANISM: Artificial Sequence
<220> FEATURE:
<223> OTHER INFORMATION: Forward primer

<400> SEQUENCE: 23
gttttcccag tcacgac                                              17

<210> SEQ ID NO 24
<211> LENGTH: 17
<212> TYPE: DNA
<213> ORGANISM: Artificial Sequence
<220> FEATURE:
<223> OTHER INFORMATION: Reverse primer

<400> SEQUENCE: 24
caggaaacag ctatgac                                              17

<210> SEQ ID NO 25
<211> LENGTH: 606
<212> TYPE: DNA
<213> ORGANISM: Homo sapiens

<400> SEQUENCE: 25
atgcacgagg gagtccacag aaaaccttcc ctcctggccc acccaggtcc cctggtgaaa    60
tcagaagaga cagtcatcct gcaatgttgg tcagatgtca ggtttgagca cttccttctg   120
cacagagagg ggaagtataa ggacactttg cacctcattg gagagcacca tgatggggtc   180
tccaaggcca acttctccat cggtcccatg atgcaagacc ttgcagggac ctacagatgc   240
tacggttctg ttactcactc ccctatcag ttgtcagctc ccagtgaccc tctggacatc    300
gtcatcacag gtctatatga aaaccttct ctctcagccc agccgggccc cacggttttg    360
gcaggagaga gcgtgacctt gtcctgcagc tcccggagct cctatgacat gtaccatcta   420
tccagggagg gggaggccca tgaacgtagg ttctctgcag ggcccaaggt caacggaaca   480
ttccaggccg actttcctct gggccctgcc acccacggag gaacctacag atgcttcggc   540
tctttccgtg actctcccta tgagtggtca aactcgagtg acccactgct tgtttctgtc   600
acatag                                                             606

<210> SEQ ID NO 26
<211> LENGTH: 201
<212> TYPE: PRT
<213> ORGANISM: Homo sapiens

<400> SEQUENCE: 26

Met His Glu Gly Val His Arg Lys Pro Ser Leu Leu Ala His Pro Gly
1               5                   10                  15

Pro Leu Val Lys Ser Glu Glu Thr Val Ile Leu Gln Cys Trp Ser Asp
            20                  25                  30

Val Arg Phe Glu His Phe Leu His Arg Glu Gly Lys Tyr Lys Asp
        35                  40                  45

Thr Leu His Leu Ile Gly Glu His His Asp Gly Val Ser Lys Ala Asn
    50                  55                  60

Phe Ser Ile Gly Pro Met Met Gln Asp Leu Ala Gly Thr Tyr Arg Cys
65                  70                  75                  80

Tyr Gly Ser Val Thr His Ser Pro Tyr Gln Leu Ser Ala Pro Ser Asp
                85                  90                  95

Pro Leu Asp Ile Val Ile Thr Gly Leu Tyr Glu Lys Pro Ser Leu Ser
            100                 105                 110

Ala Gln Pro Gly Pro Thr Val Leu Ala Gly Glu Ser Val Thr Leu Ser
            115                 120                 125

Cys Ser Ser Arg Ser Ser Tyr Asp Met Tyr His Leu Ser Arg Glu Gly
130                 135                 140

Glu Ala His Glu Arg Arg Phe Ser Ala Gly Pro Lys Val Asn Gly Thr
145                 150                 155                 160

Phe Gln Ala Asp Phe Pro Leu Gly Pro Ala Thr His Gly Gly Thr Tyr
                165                 170                 175

Arg Cys Phe Gly Ser Phe Arg Asp Ser Pro Tyr Glu Trp Ser Asn Ser
            180                 185                 190

Ser Asp Pro Leu Leu Val Ser Val Thr
            195                 200

<210> SEQ ID NO 27
<211> LENGTH: 606
<212> TYPE: DNA
<213> ORGANISM: Homo sapiens

<400> SEQUENCE: 27
atgcatgagg gagtccacag aaaaccttcc ctcctggccc acccaggtcg cctggtgaaa      60
tcagaagaga cagtcatcct gcaatgttgg tcagatgtca ggtttgagca cttccttctg     120
cacagagaag ggaagtttaa ggacactttg cacctcattg gagagcacca tgatggggtc     180
tccaaagcca acttctccat cggtcccatg atgcaagacc ttgcagggac ctacagatgc     240
tacggttctg ttactcactc ccctatcag ttgtcagctc cagtgaccc tctggacatc       300 gtcatcacag gtctatatga aaaccttct ctctcagccc agccgggccc cacggttctg      360
gcaggagaga gcgtgacctt gtcctgcagc tcccggagct cctatgacat gtaccatcta     420
tccagggagg gggaggccca tgaatgtagg ttctctgcag ggcccaaggt caacggaaca     480
ttccaggccg actttcctct gggccctgcc acccacggag gaacctacag atgcttcggc    540
tctttccgtg actctccata cgagtggtca aactcgagtg acccactgct tgtttctgtc    600
acatag                                                                606

<210> SEQ ID NO 28
<211> LENGTH: 186
<212> TYPE: PRT
<213> ORGANISM: Homo sapiens -continued

<400> SEQUENCE: 28

Met His Glu Gly Val His Arg Lys Pro Ser Leu Leu Ala His Pro Gly
1               5                   10                  15

Arg Leu Val Lys Ser Glu Glu Thr Val Ile Leu Gln Cys Trp Ser Asp
            20                  25                  30

Val Arg Phe Glu His Phe Leu Leu His Arg Glu Gly Lys Phe Lys Asp
        35                  40                  45

Thr Leu His Leu Ile Gly Glu His His Asp Gly Val Ser Lys Ala Asn
    50                  55                  60

Phe Ser Ile Gly Pro Met Met Gln Asp Leu Ala Gly Thr Tyr Arg Cys
65                  70                  75                  80

Tyr Gly Ser Val Thr His Ser Pro Tyr Gln Leu Ser Ala Pro Ser Asp
                85                  90                  95

Pro Leu Asp Ile Val Ile Thr Gly Leu Tyr Glu Lys Pro Ser Leu Ser
            100                 105                 110

Ala Gln Pro Gly Pro Thr Val Leu Ala Gly Glu Ser Val Thr Leu Ser
        115                 120                 125

Cys Ser Ser Arg Ser Ser Tyr Asp Met Tyr His Leu Ser Arg Glu Gly
    130                 135                 140

Thr Phe Gln Ala Asp Phe Pro Leu Gly Pro Ala Thr His Gly Gly Thr
145                 150                 155                 160

Tyr Arg Cys Phe Gly Ser Phe Arg Asp Ser Pro Tyr Glu Trp Ser Asn
                165                 170                 175

Ser Ser Asp Pro Leu Leu Val Ser Val Thr
            180                 185

<210> SEQ ID NO 29
<211> LENGTH: 606
<212> TYPE: DNA
<213> ORGANISM: Homo sapiens

<400> SEQUENCE: 29
atgcacgagg gagtccacag aaaaccttcc ttcctggccc acccaggtcc cctggtgaaa      60
tcagaagaga cagtcatcct gcaatgttgg tcagatgtca ggtttcagca cttccttctg     120
cacagagaag ggaagtttaa ggacactttg cacctcattg gagagcacca tgatggggtc     180
tccaaggcca acttctccat cggtcccatg atgcaagacc ttgcagggac ctacagatgc     240
tacggttctg ttactcactc cccctatcag ttgtcagctc cagtgaccc tctggacatc      300 gtcatcacag gtctatatga gaaaccttct ctctcagccc agccgggccc cacggttctg     360
gcaggagaga gcgtgacctt gtcctgcagc tcccggagct cctatgacat gtaccatcta     420
tccagggagg ggaggcccca tgaacgtagg ttctctgcag ggcccaaggt caacggaaca     480
ttccaggccg actttcctct gggccctgcc acccacggag gaacctacag atgcttcggc     540
tctttccgtg actctccata cgagtggtca aactcgagtg acccactgct tgtttctgtc     600
acatag                                                                606

<210> SEQ ID NO 30
<211> LENGTH: 201
<212> TYPE: PRT
<213> ORGANISM: Homo sapiens

<400> SEQUENCE: 30

Met His Glu Gly Val His Arg Lys Pro Ser Phe Leu Ala His Pro Gly
1               5                   10                  15

Pro Leu Val Lys Ser Glu Glu Thr Val Ile Leu Gln Cys Trp Ser Asp
            20                  25                  30

Val Arg Phe Gln His Phe Leu Leu His Arg Glu Gly Lys Phe Lys Asp
        35                  40                  45

Thr Leu His Leu Ile Gly Glu His His Asp Gly Val Ser Lys Ala Asn
    50                  55                  60

Phe Ser Ile Gly Pro Met Met Gln Asp Leu Ala Gly Thr Tyr Arg Cys
65                  70                  75                  80

Tyr Gly Ser Val Thr His Ser Pro Tyr Gln Leu Ser Ala Pro Ser Asp
                85                  90                  95

Pro Leu Asp Ile Val Ile Thr Gly Leu Tyr Glu Lys Pro Ser Leu Ser
            100                 105                 110

Ala Gln Pro Gly Pro Thr Val Leu Ala Gly Glu Ser Val Thr Leu Ser
        115                 120                 125

Cys Ser Ser Arg Ser Ser Tyr Asp Met Tyr His Leu Ser Arg Glu Gly
    130                 135                 140

Glu Ala His Glu Arg Arg Phe Ser Ala Gly Pro Lys Val Asn Gly Thr
145                 150                 155                 160

Phe Gln Ala Asp Phe Pro Leu Gly Pro Ala Thr His Gly Gly Thr Tyr
                165                 170                 175

Arg Cys Phe Gly Ser Phe Arg Asp Ser Pro Tyr Glu Trp Ser Asn Ser
            180                 185                 190

Ser Asp Pro Leu Leu Val Ser Val Thr
        195                 200

<210> SEQ ID NO 31
<211> LENGTH: 22
<212> TYPE: DNA
<213> ORGANISM: Artificial
<220> FEATURE:
<223> OTHER INFORMATION: VL Forward primer

<400> SEQUENCE: 31
racattgtsh tgacycagtc tc                                        22

<210> SEQ ID NO 32
<211> LENGTH: 20
<212> TYPE: DNA
<213> ORGANISM: Artificial
<220> FEATURE:
<223> OTHER INFORMATION: VL Forward primer

<400> SEQUENCE: 32
gaaactgtga tgacccagtc                                           20

<210> SEQ ID NO 33
<211> LENGTH: 19
<212> TYPE: DNA
<213> ORGANISM: Artificial
<220> FEATURE:
<223> OTHER INFORMATION: VL Forward primer

<400> SEQUENCE: 33
caggctgttg tgactcagg                                            19

```
<210> SEQ ID NO 34
<211> LENGTH: 20
<212> TYPE: DNA
<213> ORGANISM: Artificial
<220> FEATURE:
<223> OTHER INFORMATION: VL Forward primer

<400> SEQUENCE: 34
gamactryds tgacccagtc                                                   20

<210> SEQ ID NO 35
<211> LENGTH: 21
<212> TYPE: DNA
<213> ORGANISM: Artificial
<220> FEATURE:
<223> OTHER INFORMATION: VL Forward primer

<400> SEQUENCE: 35
racrtccagw tracccagwc t                                                 21

<210> SEQ ID NO 36
<211> LENGTH: 20
<212> TYPE: DNA
<213> ORGANISM: Artificial
<220> FEATURE:
<223> OTHER INFORMATION: VL Forward primer

<400> SEQUENCE: 36
gacatccaya tgacwcagwm                                                   20

<210> SEQ ID NO 37
<211> LENGTH: 20
<212> TYPE: DNA
<213> ORGANISM: Artificial
<220> FEATURE:
<223> OTHER INFORMATION: VL Forward primer

<400> SEQUENCE: 37
gayatccrgr tgacwcagtc                                                   20

<210> SEQ ID NO 38
<211> LENGTH: 22
<212> TYPE: DNA
<213> ORGANISM: Artificial
<220> FEATURE:
<223> OTHER INFORMATION: VL Forward primer

<400> SEQUENCE: 38
gacatysrga tgacymagtc tc                                                22

<210> SEQ ID NO 39
<211> LENGTH: 22
<212> TYPE: DNA
<213> ORGANISM: Artificial
<220> FEATURE:
<223> OTHER INFORMATION: VL Forward primer

<400> SEQUENCE: 39
gacatytkga tgacymagtc tc                                                22

<210> SEQ ID NO 40
<211> LENGTH: 21
<212> TYPE: DNA
<213> ORGANISM: Artificial
<220> FEATURE:
<223> OTHER INFORMATION: VL Forward primer
```

<400> SEQUENCE: 40
gacattkyga tracccartm t                                              21

<210> SEQ ID NO 41
<211> LENGTH: 20
<212> TYPE: DNA
<213> ORGANISM: Artificial
<220> FEATURE:
<223> OTHER INFORMATION: VL Forward primer

<400> SEQUENCE: 41
gatattgtga tgachcarrs                                                20

<210> SEQ ID NO 42
<211> LENGTH: 22
<212> TYPE: DNA
<213> ORGANISM: Artificial
<220> FEATURE:
<223> OTHER INFORMATION: VL Forward primer

<400> SEQUENCE: 42
gatgttgtgw tgacacaaac tc                                             22

<210> SEQ ID NO 43
<211> LENGTH: 20
<212> TYPE: DNA
<213> ORGANISM: Artificial
<220> FEATURE:
<223> OTHER INFORMATION: VL Forward primer

<400> SEQUENCE: 43
gatgttgttt tggtgacaca                                                20

<210> SEQ ID NO 44
<211> LENGTH: 18
<212> TYPE: DNA
<213> ORGANISM: Artificial
<220> FEATURE:
<223> OTHER INFORMATION: VL Forward primer

<400> SEQUENCE: 44
gatgttgtga tgacccag                                                  18

<210> SEQ ID NO 45
<211> LENGTH: 20
<212> TYPE: DNA
<213> ORGANISM: Artificial
<220> FEATURE:
<223> OTHER INFORMATION: VL Forward primer

<400> SEQUENCE: 45
gatgttrtgm tgrcccagac                                                20

<210> SEQ ID NO 46
<211> LENGTH: 22
<212> TYPE: DNA
<213> ORGANISM: Artificial
<220> FEATURE:
<223> OTHER INFORMATION: VL Forward primer

<400> SEQUENCE: 46
gamattgtgm tsayycagtc tc                                             22

```
<210> SEQ ID NO 47
<211> LENGTH: 21
<212> TYPE: DNA
<213> ORGANISM: Artificial
<220> FEATURE:
<223> OTHER INFORMATION: VL Forward primer

<400> SEQUENCE: 47
gamattrtrc tvacccagtc t                                              21

<210> SEQ ID NO 48
<211> LENGTH: 20
<212> TYPE: DNA
<213> ORGANISM: Artificial
<220> FEATURE:
<223> OTHER INFORMATION: VL Forward primer

<400> SEQUENCE: 48
gawawtgtkc tmmctcagtc                                                20

<210> SEQ ID NO 49
<211> LENGTH: 20
<212> TYPE: DNA
<213> ORGANISM: Artificial
<220> FEATURE:
<223> OTHER INFORMATION: VL Forward primer

<400> SEQUENCE: 49
gacgttgtgc tgactcagtc                                                20

<210> SEQ ID NO 50
<211> LENGTH: 22
<212> TYPE: DNA
<213> ORGANISM: Artificial
<220> FEATURE:
<223> OTHER INFORMATION: VL Forward primer

<400> SEQUENCE: 50
gayatcrtkh tractcagtc tc                                             22

<210> SEQ ID NO 51
<211> LENGTH: 18
<212> TYPE: DNA
<213> ORGANISM: Artificial
<220> FEATURE:
<223> OTHER INFORMATION: VL Forward primer

<400> SEQUENCE: 51
cagcccgtgc tgcatcag                                                  18

<210> SEQ ID NO 52
<211> LENGTH: 20
<212> TYPE: DNA
<213> ORGANISM: Artificial
<220> FEATURE:
<223> OTHER INFORMATION: VL Forward primer

<400> SEQUENCE: 52
cagwtcacgc tsacycarcm                                                20

<210> SEQ ID NO 53
<211> LENGTH: 20
<212> TYPE: DNA
<213> ORGANISM: Artificial
<220> FEATURE:
<223> OTHER INFORMATION: VL Forward primer
```

```
<400> SEQUENCE: 53
cagkytgtsc ttactcagyc                                          20

<210> SEQ ID NO 54
<211> LENGTH: 20
<212> TYPE: DNA
<213> ORGANISM: Artificial
<220> FEATURE:
<223> OTHER INFORMATION: VL Forward primer

<400> SEQUENCE: 54
actggagaaa caacacagtc                                          20

<210> SEQ ID NO 55
<211> LENGTH: 19
<212> TYPE: DNA
<213> ORGANISM: Artificial
<220> FEATURE:
<223> OTHER INFORMATION: VL Forward primer

<400> SEQUENCE: 55
actgtggcct tagagcagg                                           19

<210> SEQ ID NO 56
<211> LENGTH: 20
<212> TYPE: DNA
<213> ORGANISM: Artificial
<220> FEATURE:
<223> OTHER INFORMATION: VL Forward primer

<400> SEQUENCE: 56
agctatgagc tgatccaacc                                          20

<210> SEQ ID NO 57
<211> LENGTH: 20
<212> TYPE: DNA
<213> ORGANISM: Artificial
<220> FEATURE:
<223> OTHER INFORMATION: VL Reverse primer

<400> SEQUENCE: 57
acstttcary tccwgcytgg                                          20

<210> SEQ ID NO 58
<211> LENGTH: 22
<212> TYPE: DNA
<213> ORGANISM: Artificial
<220> FEATURE:
<223> OTHER INFORMATION: VL Reverse primer

<400> SEQUENCE: 58
acgtttyatt tccarctksg tc                                       22

<210> SEQ ID NO 59
<211> LENGTH: 22
<212> TYPE: DNA
<213> ORGANISM: Artificial
<220> FEATURE:
<223> OTHER INFORMATION: VL Reverse primer

<400> SEQUENCE: 59
abstttgatc tccagyttgg tc                                       22
```

```
<210> SEQ ID NO 60
<211> LENGTH: 23
<212> TYPE: DNA
<213> ORGANISM: Artificial
<220> FEATURE:
<223> OTHER INFORMATION: VL Reverse primer

<400> SEQUENCE: 60
taggacagts agyktkgttc cwc                                               23

<210> SEQ ID NO 61
<211> LENGTH: 15
<212> TYPE: DNA
<213> ORGANISM: Artificial
<220> FEATURE:
<223> OTHER INFORMATION: VL Reverse primer

<400> SEQUENCE: 61
ccggctttca ggcag                                                        15

<210> SEQ ID NO 62
<211> LENGTH: 30
<212> TYPE: DNA
<213> ORGANISM: Artificial
<220> FEATURE:
<223> OTHER INFORMATION: VL Reverse primer

<400> SEQUENCE: 62
ctcattcctg ttgaagctct tgacgacggg                                        30

<210> SEQ ID NO 63
<211> LENGTH: 33
<212> TYPE: DNA
<213> ORGANISM: Artificial
<220> FEATURE:
<223> OTHER INFORMATION: VL Reverse primer

<400> SEQUENCE: 63
acactcagca cgggacaaac tcttctccac agt                                    33

<210> SEQ ID NO 64
<211> LENGTH: 33
<212> TYPE: DNA
<213> ORGANISM: Artificial
<220> FEATURE:
<223> OTHER INFORMATION: VL Reverse primer

<400> SEQUENCE: 64
acactctgca ggagacagac tcttttccac agt                                    33

<210> SEQ ID NO 65
<211> LENGTH: 22
<212> TYPE: DNA
<213> ORGANISM: Artificial
<220> FEATURE:
<223> OTHER INFORMATION: VH Forward primer

<400> SEQUENCE: 65
aggtrcarct ramrgagtca gg                                                22

<210> SEQ ID NO 66
<211> LENGTH: 19
<212> TYPE: DNA
<213> ORGANISM: Artificial
<220> FEATURE:
<223> OTHER INFORMATION: VH Forward primer
```

<400> SEQUENCE: 66
aggtgsakmt gaaggagwc                                                19

<210> SEQ ID NO 67
<211> LENGTH: 19
<212> TYPE: DNA
<213> ORGANISM: Artificial
<220> FEATURE:
<223> OTHER INFORMATION: VH Forward primer

<400> SEQUENCE: 67
argtgcagyk gawggagtc                                                19

<210> SEQ ID NO 68
<211> LENGTH: 20
<212> TYPE: DNA
<213> ORGANISM: Artificial
<220> FEATURE:
<223> OTHER INFORMATION: VH Forward primer

<400> SEQUENCE: 68
aggthcagct gcascartct                                               20

<210> SEQ ID NO 69
<211> LENGTH: 20
<212> TYPE: DNA
<213> ORGANISM: Artificial
<220> FEATURE:
<223> OTHER INFORMATION: VH Forward primer

<400> SEQUENCE: 69
aggthcagct gtaccartct                                               20

<210> SEQ ID NO 70
<211> LENGTH: 19
<212> TYPE: DNA
<213> ORGANISM: Artificial
<220> FEATURE:
<223> OTHER INFORMATION: VH Forward primer

<400> SEQUENCE: 70
agatccagtt ggyacagtc                                                19

<210> SEQ ID NO 71
<211> LENGTH: 19
<212> TYPE: DNA
<213> ORGANISM: Artificial
<220> FEATURE:
<223> OTHER INFORMATION: VH Forward primer

<400> SEQUENCE: 71
aggcccagct gcagtctgg                                                19

<210> SEQ ID NO 72
<211> LENGTH: 19
<212> TYPE: DNA
<213> ORGANISM: Artificial
<220> FEATURE:
<223> OTHER INFORMATION: VH Forward primer

<400> SEQUENCE: 72
aggtccagyt gcagcarts                                                19

```
<210> SEQ ID NO 73
<211> LENGTH: 19
<212> TYPE: DNA
<213> ORGANISM: Artificial
<220> FEATURE:
<223> OTHER INFORMATION: VH Forward primer

<400> SEQUENCE: 73
agattcagct gcarcagtg                                              19

<210> SEQ ID NO 74
<211> LENGTH: 22
<212> TYPE: DNA
<213> ORGANISM: Artificial
<220> FEATURE:
<223> OTHER INFORMATION: VH Forward primer

<400> SEQUENCE: 74
aaacagtcca gctacagcag tc                                          22

<210> SEQ ID NO 75
<211> LENGTH: 22
<212> TYPE: DNA
<213> ORGANISM: Artificial
<220> FEATURE:
<223> OTHER INFORMATION: VH Forward primer

<400> SEQUENCE: 75
aagargtccw gctgcakcag tm                                          22

<210> SEQ ID NO 76
<211> LENGTH: 19
<212> TYPE: DNA
<213> ORGANISM: Artificial
<220> FEATURE:
<223> OTHER INFORMATION: VH Forward primer

<400> SEQUENCE: 76
aggttmmtct gmaasagtc                                              19

<210> SEQ ID NO 77
<211> LENGTH: 19
<212> TYPE: DNA
<213> ORGANISM: Artificial
<220> FEATURE:
<223> OTHER INFORMATION: VH Forward primer

<400> SEQUENCE: 77
argtyaasct rcwgcagtc                                              19

<210> SEQ ID NO 78
<211> LENGTH: 22
<212> TYPE: DNA
<213> ORGANISM: Artificial
<220> FEATURE:
<223> OTHER INFORMATION: VH Forward primer

<400> SEQUENCE: 78
aagaggtaaa gctgcarcag tc                                          22

<210> SEQ ID NO 79
<211> LENGTH: 22
<212> TYPE: DNA
<213> ORGANISM: Artificial
<220> FEATURE:
<223> OTHER INFORMATION: VH Forward primer
```

<400> SEQUENCE: 79
aagargttca rctgcagcag tc                                          22

<210> SEQ ID NO 80
<211> LENGTH: 22
<212> TYPE: DNA
<213> ORGANISM: Artificial
<220> FEATURE:
<223> OTHER INFORMATION: VH Forward primer

<400> SEQUENCE: 80
aagaggtgca rmttcwggag wc                                          22

<210> SEQ ID NO 81
<211> LENGTH: 22
<212> TYPE: DNA
<213> ORGANISM: Artificial
<220> FEATURE:
<223> OTHER INFORMATION: VH Forward primer

<400> SEQUENCE: 81
aagaggtgca rmttttggag wc                                          22

<210> SEQ ID NO 82
<211> LENGTH: 22
<212> TYPE: DNA
<213> ORGANISM: Artificial
<220> FEATURE:
<223> OTHER INFORMATION: VH Forward primer

<400> SEQUENCE: 82
aagaggtgaa acttgtcgag tc                                          22

<210> SEQ ID NO 83
<211> LENGTH: 22
<212> TYPE: DNA
<213> ORGANISM: Artificial
<220> FEATURE:
<223> OTHER INFORMATION: VH Forward primer

<400> SEQUENCE: 83
aagvggtgca gctwgtkgag wc                                          22

<210> SEQ ID NO 84
<211> LENGTH: 22
<212> TYPE: DNA
<213> ORGANISM: Artificial
<220> FEATURE:
<223> OTHER INFORMATION: VH Forward primer

<400> SEQUENCE: 84
aagargtgca rytggtggar tc                                          22

<210> SEQ ID NO 85
<211> LENGTH: 25
<212> TYPE: DNA
<213> ORGANISM: Artificial
<220> FEATURE:
<223> OTHER INFORMATION: VH Forward primer

<400> SEQUENCE: 85
aagaagtgaa rctggwrgar tctgg                                       25

```
<210> SEQ ID NO 86
<211> LENGTH: 25
<212> TYPE: DNA
<213> ORGANISM: Artificial
<220> FEATURE:
<223> OTHER INFORMATION: VH Forward primer

<400> SEQUENCE: 86
aagaagtgaa rctgttrgar tctgg                                    25

<210> SEQ ID NO 87
<211> LENGTH: 22
<212> TYPE: DNA
<213> ORGANISM: Artificial
<220> FEATURE:
<223> OTHER INFORMATION: VH Forward primer

<400> SEQUENCE: 87
aagmrgtaca gctrgtkgag tc                                       22

<210> SEQ ID NO 88
<211> LENGTH: 22
<212> TYPE: DNA
<213> ORGANISM: Artificial
<220> FEATURE:
<223> OTHER INFORMATION: VH Forward primer

<400> SEQUENCE: 88
aagaggtgca gctgaaggaa tc                                       22

<210> SEQ ID NO 89
<211> LENGTH: 20
<212> TYPE: DNA
<213> ORGANISM: Artificial
<220> FEATURE:
<223> OTHER INFORMATION: VH Reverse primer

<400> SEQUENCE: 89
kgaggasacg gtgaccrkgg                                          20

<210> SEQ ID NO 90
<211> LENGTH: 20
<212> TYPE: DNA
<213> ORGANISM: Artificial
<220> FEATURE:
<223> OTHER INFORMATION: VH Reverse primer

<400> SEQUENCE: 90
tgaggagact gtgagagtgg                                          20

<210> SEQ ID NO 91
<211> LENGTH: 21
<212> TYPE: DNA
<213> ORGANISM: Artificial
<220> FEATURE:
<223> OTHER INFORMATION: VH Reverse primer

<400> SEQUENCE: 91
tgargagact rtgrycrtga c                                        21

<210> SEQ ID NO 92
<211> LENGTH: 20
<212> TYPE: DNA
<213> ORGANISM: Artificial
<220> FEATURE:
<223> OTHER INFORMATION: VH Reverse primer
```

```
<400> SEQUENCE: 92
tgargagaca gwgacyrrag                                              20

<210> SEQ ID NO 93
<211> LENGTH: 14
<212> TYPE: PRT
<213> ORGANISM: Artificial Sequence
<220> FEATURE:
<223> OTHER INFORMATION: CDR3
<220> FEATURE:
<221> NAME/KEY: misc_feature
<222> LOCATION: (2)..(8)
<223> OTHER INFORMATION: X = any amino acid

<400> SEQUENCE: 93

Thr Xaa Xaa Xaa Xaa Xaa Xaa Xaa Tyr Tyr Val Met Asp Ala
1               5                   10

<210> SEQ ID NO 94
<211> LENGTH: 15
<212> TYPE: PRT
<213> ORGANISM: Artificial Sequence
<220> FEATURE:
<223> OTHER INFORMATION: CDR3
<220> FEATURE:
<221> NAME/KEY: misc_feature
<222> LOCATION: (2)..(9)
<223> OTHER INFORMATION: X = any amino acid

<400> SEQUENCE: 94

Thr Xaa Xaa Xaa Xaa Xaa Xaa Xaa Xaa Tyr Tyr Val Met Asp Ala
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: CDR3
<220> FEATURE:
<221> NAME/KEY: misc_feature
<222> LOCATION: (2)..(10)
<223> OTHER INFORMATION: X = any amino acid

<400> SEQUENCE: 95

Thr Xaa Xaa Xaa Xaa Xaa Xaa Xaa Xaa Xaa Tyr Tyr Val Met Asp Ala
1               5                   10                  15
```

MONOCLONAL ANTIBODIES AGAINST KIR2DS1

TECHNICAL FIELD

The present disclosure relates to a monoclonal antibody to KIR2DS1 or a fragment comprising an antigen-binding region thereof, a nucleic acid, an expression vector, a transformant, a method of producing the monoclonal antibody or the fragment comprising an antigen-binding region thereof, a cell that produces the monoclonal antibody or the fragment comprising an antigen-binding region thereof, a pharmaceutical composition, a method for screening a substance that binds to KIR2DL1, a method for detecting KIR2DS1 in a sample, and a method for measuring a population of KIR2DS1 and KIR2DL1 in a sample.

BACKGROUND ART

Natural killer (NK) cells play an important role in controlling cancer, infectious diseases, transplant rejection, autoimmune diseases, and the like. Receptor molecules, namely killer cell immunoglobulin-like receptors (hereinafter, referred to as KIRs) are present on the surface of NK cells. KIRs are very highly polymorphic and make up one of the paired receptor family which is a family consisting of inhibitory type receptors and activating type receptors. The activation of NK cells depends on a ratio of expression level of inhibitory type KIRs and activating type KIRs and the presence of ligands on target cells. Further, the KIR family share high sequence homology in the extracellular domain; and it is often the case that the inhibitory type KIR and the activating type KIR recognize an identical ligand.

KIR2DS1 which is the activating type KIR makes up the paired receptor family with KIR2DL1 which is the inhibitory type KIR. KIR2DS1 controls the activation of NK cells by recognizing some HLA-Cs, which are the same ligands as KIR2DL1, and unknown non-self ligands.

Virus-infected cells and tumor cells express the KIR2DS1 ligand and are thereby recognized by NK cells; and activated NK cells try to remove those virus-infected cells and tumor cells. Meanwhile, an inappropriate immune response originating from excessive activation of NK cells is involved in autoimmune diseases and transplant rejection.

For the purpose of activating NK cells, clinical applications using an antibody that recognizes the inhibitory type KIR have been under way; and several reports have come out.

Patent Literature 1 to 3 disclose an antibody that binds to KIR2DL1, KIR2DL2, and KIR2DL3. In addition, Non Patent Literature 1 to 3 disclose an antibody that binds to KIR2DL1, KIR2DL2, and KIR2DL3 to exhibit inhibitory effects, namely IPH2101. To be more specific, Non Patent Literature 1 describes a phase I clinical trial of IPH2101 for acute myeloid leukemia; Non Patent Literature 2 describes a phase I clinical trial of IPH2101 for multiple myeloma; and Non Patent Literature 3 describes combined effects of IPH2101 and lenalidomide on multiple myeloma. In addition, Non Patent Literature 4 and 5 disclose an antibody that binds to KIR2DL1, KIR2DL2, and KIR2DL3 to exhibit inhibitory effects, namely 1-7F9.

CITATION LIST

Patent Literature

Patent Literature 1: National Patent Publication No. 2007-524612

Patent Literature 2: National Patent Publication No. 2008-506368

Patent Literature 3: National Patent Publication No. 2008-526812

Non Patent Literature

Non Patent Literature 1: Norbert Vey et al, Blood 2012 120:4317-4323

Non Patent Literature 2: Don M. Benson Jr et al, Blood 2012 120:4324-4333

Non Patent Literature 3: Don M. Benson Jr et al, Blood 2011 118:6387-6391

Non Patent Literature 4: Susanne E. Johansson et al, Clinical Immunology (2010) 134, 158-168

Non Patent Literature 5: Francois Romagne et al, Blood 2009 114:2667-2677

SUMMARY OF INVENTION

Technical Problem

The antibodies described in Patent Literature 1 to 3 and Non Patent Literature 1 to 5, however, extensively inhibit inhibitory type KIRs which inherently function so as not to attack self cells; and therefore incidence of adverse effects including induction of autoimmune response is a concern. In addition, there have thus far been no reports concerning an antibody that specifically binds to KIR2DS1.

The present disclosure has been made in view of the above circumstances; and an object thereof is to provide a novel monoclonal antibody to KIR2DS1 or a fragment comprising an antigen-binding region thereof, a nucleic acid, an expression vector, a transformant, a method of producing the monoclonal antibody or the fragment comprising an antigen-binding region thereof, a cell that produces the monoclonal antibody or the fragment comprising an antigen-binding region thereof, a pharmaceutical composition, a method for screening a substance that binds to KIR2DL1, a method for detecting KIR2DS1 in a sample, and a method for measuring a population of KIR2DS1 and KIR2DL1 in a sample.

Solution to Problem

In order to accomplish the above object, a monoclonal antibody to KIR2DS1 or a fragment comprising an antigen-binding region thereof according to a first aspect of the present disclosure includes:

VL having an amino acid sequence of SEQ ID NO: 1 or an amino acid sequence having the same amino acid sequence as the amino acid sequence except that one or several amino acids are conservatively substituted as CDR1, having an amino acid sequence of SEQ ID NO: 2 or an amino acid sequence having the same amino acid sequence as the amino acid sequence except that one or several amino acids are conservatively substituted as CDR2, and having an amino acid sequence of SEQ ID NO: 3 or an amino acid sequence having the same amino acid sequence as the amino acid sequence except that one or several amino acids are conservatively substituted as CDR3; and VH having an amino acid sequence of SEQ ID NO: 4 or SEQ ID NO: 5 or an amino acid sequence having the same amino acid sequence as the amino acid sequence except that one or several amino acids are conservatively substituted as CDR1, having an amino acid sequence of SEQ ID NO: 6 or an amino acid sequence having the same amino acid sequence as the amino acid sequence except that one or several amino acids are conservatively substituted as CDR2, and having an amino acid sequence of any one selected from the group consisting of SEQ ID NO: 7, SEQ ID NO: 8, and SEQ ID NO: 9 or an amino acid sequence having the same amino acid sequence as the amino acid sequence except that one or several amino acids are conservatively substituted as CDR3.

VH comprises, for example, an amino acid sequence of SEQ ID NO: 4 or an amino acid sequence having the same amino acid sequence as the amino acid sequence except that one or several amino acids are conservatively substituted as CDR1, comprises an amino acid sequence of SEQ ID NO: 6 or an amino acid sequence having the same amino acid sequence as the amino acid sequence except that one or several amino acids are conservatively substituted as CDR2, and comprises an amino acid sequence of SEQ ID NO: 7 or an amino acid sequence having the same amino acid sequence as the amino acid sequence except that one or several amino acids are conservatively substituted as CDR3.

VH comprises, for example, an amino acid sequence of SEQ ID NO: 5 or an amino acid sequence having the same amino acid sequence as the amino acid sequence except that one or several amino acids are conservatively substituted as CDR1, comprises an amino acid sequence of SEQ ID NO: 6 or an amino acid sequence having the same amino acid sequence as the amino acid sequence except that one or several amino acids are conservatively substituted as CDR2, and comprises an amino acid sequence of SEQ ID NO: 8 or an amino acid sequence having the same amino acid sequence as the amino acid sequence except that one or several amino acids are conservatively substituted as CDR3.

VH comprises, for example, an amino acid sequence of SEQ ID NO: 5 or an amino acid sequence having the same amino acid sequence as the amino acid sequence except that one or several amino acids are conservatively substituted as CDR1, comprises an amino acid sequence of SEQ ID NO: 6 or an amino acid sequence having the same amino acid sequence as the amino acid sequence except that one or several amino acids are conservatively substituted as CDR2, and comprises an amino acid sequence of SEQ ID NO: 9 or an amino acid sequence having the same amino acid sequence as the amino acid sequence except that one or several amino acids are conservatively substituted as CDR3.

A monoclonal antibody to KIR2DS1 or a fragment comprising an antigen-binding region thereof according to a second aspect of the present disclosure is produced by at least one hybridoma selected from the group consisting of a hybridoma with Accession No. NITE BP-01853, a hybridoma with Accession No. NITE BP-01855, and a hybridoma with Accession No. NITE BP-01854.

The monoclonal antibody to KIR2DS1 or the fragment comprising an antigen-binding region thereof according to the first and second aspect of the present disclosure is, for example, a chimeric antibody or a humanized antibody.

A nucleic acid according to a third aspect of the present disclosure comprises a base sequence encoding the monoclonal antibody to KIR2DS1 or the fragment comprising an antigen-binding region thereof according to the first and second aspect of the present disclosure.

An expression vector according to a fourth aspect of the present disclosure comprises the nucleic acid according to the third aspect of the present disclosure.

A transformant producing the monoclonal antibody to KIR2DS1 or the fragment comprising an antigen-binding region thereof according to the first and second aspect of the present disclosure according to a fifth aspect of the present disclosure comprises the nucleic acid according to the third aspect of the present disclosure or the expression vector according to the fourth aspect of the present disclosure.

A method of producing the monoclonal antibody to KIR2DS1 or the fragment comprising an antigen-binding region thereof according to the first and second aspect of the present disclosure according to a sixth aspect of the present disclosure comprises a step of culturing the transformant according to the fifth aspect of the present disclosure to collect the antibody or the fragment comprising an antigen-binding region thereof from a culture.

A cell according to a seventh aspect of the present disclosure produces the monoclonal antibody to KIR2DS1 or the fragment comprising an antigen-binding region thereof according to the first and second aspect of the present disclosure.

The cell is at least one hybridoma selected from the group consisting of, for example, a hybridoma with Accession No. NITE BP-01853, a hybridoma with Accession No. NITE BP-01855, and a hybridoma with Accession No. NITE BP-01854.

A pharmaceutical composition according to an eighth aspect of the present disclosure comprises the monoclonal antibody to KIR2DS1 or the fragment comprising an antigen-binding region thereof according to the first and second aspect of the present disclosure.

The monoclonal antibody to KIR2DS1 or the fragment comprising an antigen-binding region thereof according to the first and second aspect of the present disclosure acts as, for example, an agonist.

The monoclonal antibody to KIR2DS1 or the fragment comprising an antigen-binding region thereof according to the first and second aspect of the present disclosure acts as, for example, an antagonist.

The monoclonal antibody to KIR2DS1 or the fragment comprising an antigen-binding region thereof according to the first and second aspect of the present disclosure, for example, neither acts as an agonist for KIR2DS1 nor acts as an antagonist against KIR2DS1.

A method for screening a substance that binds to KIR2DL1 according to a ninth aspect of the present disclosure comprises:

a step of administering the monoclonal antibody or the fragment comprising an antigen-binding region thereof according to the first and second aspect of the present disclosure that neither acts as an agonist for KIR2DS1 nor acts as an antagonist against KIR2DS1 to a cell population;

a step of measuring the level A of KIR2DL1 activity in the above cell population;

a step of administering a candidate substance to the above cell population;

a step of measuring the level B of KIR2DL1 activity after administering the above candidate substance to the above cell population; and a step of comparing the above level A with the above level B.

A method for detecting KIR2DS1 in a sample according to a tenth aspect of the present disclosure comprises:

a step of bringing the monoclonal antibody to KIR2DS1 or the fragment comprising an antigen-binding region thereof according to the first and second aspect of the present disclosure into contact with a sample from a subject; and a step of determining whether or not the above monoclonal antibody or the above fragment comprising an antigen-binding region thereof binds to KIR2DS1 in the above sample.

A method for measuring a population of KIR2DS1 and KIR2DL1 in a sample according to an eleventh aspect of the present disclosure comprises:

a step of bringing the monoclonal antibody to KIR2DS1 or the fragment comprising an antigen-binding region thereof according to the first and second aspect of the present disclosure into contact with a sample from a subject to measure the amount of KIR2DS1 in the above sample; and a step of measuring the amount of KIR2DL1 in the above sample.

Advantageous Effects of Invention

According to the present disclosure, it is possible to provide a novel monoclonal antibody to KIR2DS1 or a fragment comprising an antigen-binding region thereof, a nucleic acid, an expression vector, a transformant, a method of producing the monoclonal antibody or the fragment comprising an antigen-binding region thereof, a cell that produces the monoclonal antibody or the fragment comprising an antigen-binding region thereof, a pharmaceutical composition, a method for screening a substance that binds to KIR2DL1, a method for detecting KIR2DS1 in a sample, and a method for measuring a population of KIR2DS1 and KIR2DL1 in a sample.

BRIEF DESCRIPTION OF DRAWINGS

FIG. 1A is a figure showing the result of ELISA for 1C7B8-G3; FIG. 1B is for 1C7H12-B1; FIG. 1C is for 1C7B8-E1, and FIG. 1D is for 1C7H12-E4;

FIG. 2A is a figure showing the result of ELISA for 3E11A5-E10; FIG. 2B is for 3E11A5-G6; FIG. 2C is for 5B12D2-B3, and FIG. 2D is for 5B12D2-A4;

FIG. 3A is a figure showing the result of SPR for 1C7B8-G3; FIG. 3B is for 1C7H12-B1; FIG. 3C is for 1C7B8-E1, and FIG. 3D is for 1C7H12-E4; FIG. 4A is a figure showing the result of SPR for 3E11A5-E10; FIG. 4B is for 3E11A5-G6; FIG. 4C is for 5B12D2-B3, and FIG. 4D is for 5B12D2-A4.

DESCRIPTION OF EMBODIMENTS

Figure 1:
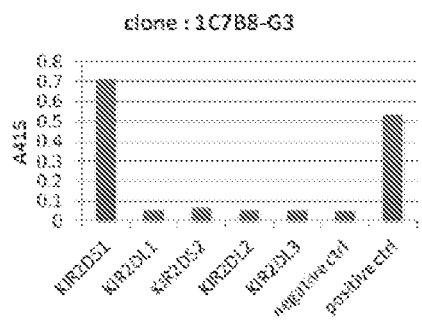
FIG. 1 is a figure showing the results of ELISA.
Figure 1:
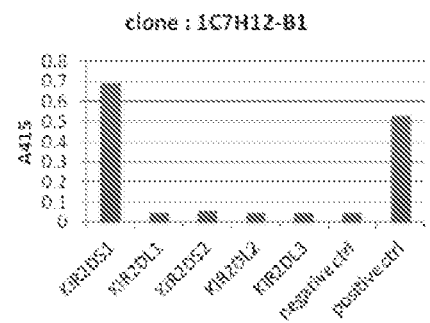
Figure 1:
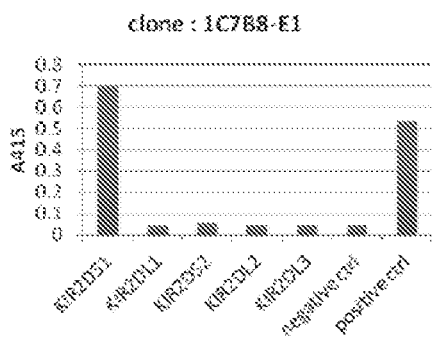
Figure 1:
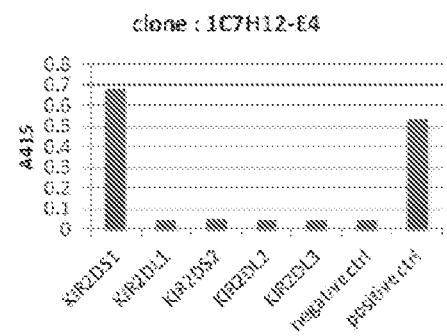

First, the monoclonal antibody and the fragment comprising an antigen-binding region thereof according to the present disclosure will be described in detail.

In the present specification, "VL" means a light chain and "VH" means a heavy chain. Further, "CDR1" means the first complementarity determining region of VL or VH; "CDR2" means the second complementarity determining region of VL or VH; and "CDR3" means the third complementarity determining region of VL or VH.

The monoclonal antibody according to the present disclosure is a monoclonal antibody to KIR2DS1, that is, a monoclonal antibody that specifically binds to KIR2DS1. Here, the phrase "to specifically bind" means that the antibody binds to KIR2DS1 with a higher affinity than to other proteins or peptides. Here, the term "high affinity" means a binding affinity is high to such an extent that KIR2DS1 can be distinguished from the proteins or peptides to be detected by using a method known in the art. A dissociation constant (Kd) in this case is, for example, at least not more than $1\times10^{-7}$ M, preferably at least not more than $1\times10^{-8}$ M, or more preferably not more than $1\times10^{-9}$ M, or smaller.

The property of the monoclonal antibody according to the present disclosure to bind to KIR2DS1 can be evaluated by a method known in the art; and the binding property can be evaluated, for example, by enzyme-linked immunosorbent assay (ELISA), surface plasmon resonance (SPR), or the like.

The monoclonal antibody according to the present disclosure specifically binds to KIR2DS1 but does not bind to other KIRs, namely KIR2DL1, KIR2DS2, KIR2DL2, and KIR2DL3.

In the present specification, the term "a fragment comprising an antigen-binding region thereof" means a fragment that contains the antigen-binding region a monoclonal antibody to KIR2DS1, examples of which include Fab, Fab', F(ab')2, and a single chain antibody (scFv). Therefore, like the whole monoclonal antibody, "a fragment comprising an antigen-binding region thereof" is also capable of specifically binding to KIR2DS1. In cases where such a fragment is prepared, a preparation method known to those skilled in the art can be used; and examples thereof include a method comprising digesting an antibody by a conventional method using a proteolytic enzyme (for example, pepsin, papain, or the like) and purifying the resultant by a known method of protein separation and purification and a preparation method by gene recombination.

In the present specification, it is hereinafter understood that "the monoclonal antibody according to the present disclosure" or "the monoclonal antibody of the present disclosure" includes a fragment that contains the antigen-binding region of the monoclonal antibody according to the present disclosure.

The monoclonal antibody according to the present disclosure has:

VL comprising an amino acid sequence of SEQ ID NO: 1 as CDR1, comprising an amino acid sequence of SEQ ID NO: 2 as CDR2, and comprising an amino acid sequence of SEQ ID NO: 3 as CDR3; and VH comprising an amino acid sequence of SEQ ID NO: 4 or SEQ ID NO: 5 as CDR1, comprising an amino acid sequence of SEQ ID NO: 6 as CDR2, and comprising an amino acid sequence of any one selected from the group consisting of SEQ ID NO: 7, SEQ ID NO: 8, and SEQ ID NO: 9 as CDR3.

Preferably, the VH of the monoclonal antibody according to the present disclosure comprises the amino acid sequence of SEQ ID NO: 4 as CDR1, comprises the amino acid sequence of SEQ ID NO: 6 as CDR2, and comprises the amino acid sequence of SEQ ID NO: 7 as CDR3. These clones are, in the present specification, denoted as 1C7B8-G3, 1C7H12-B1, 1C7B8-E1, and 1C7H12-E4 (Table 1).

Further, the VH of the monoclonal antibody according to the present disclosure preferably comprises the amino acid sequence of SEQ ID NO: 5 as CDR1, comprises the amino acid sequence of SEQ ID NO: 6 as CDR2, and comprises the amino acid sequence of SEQ ID NO: 8 as CDR3. These clones are, in the present specification, denoted as 3E11A5-E10 and 3E11A5-G6 (Table 1).

Further, the VH of the monoclonal antibody according to the present disclosure preferably comprises the amino acid sequence of SEQ ID NO: 5 as CDR1, comprises the amino acid sequence of SEQ ID NO: 6 as CDR2, and comprises the amino acid sequence of SEQ ID NO: 9 as CDR3. These clones are, in the present specification, denoted as 5B12D2-B3 and 5B12D2-A4 (Table 1).

TABLE 1

| | VL | | |
|---|---|---|---|
| | CDR1 | CDR2 | CDR3 |
| 1C7B8-G3<br>1C7H12-B1<br>1C7B8-E1<br>1C7H12-E4<br>3E11A5-E10<br>3E11A5-G6<br>5B12D2-B3<br>5B12D2-A4 | KASQNVGSNVD<br>(SEQ ID NO: 1) | KASNRYT<br>(SEQ ID NO: 2) | MQSNTNPLT<br>(SEQ ID NO: 3) |

| | VH | | |
|---|---|---|---|
| | CDR1 | CDR2 | CDR3 |
| 1C7B8-G3<br>1C7H12-B1<br>1C7B8-E1<br>1C7H12-E4 | GFSLSTYSMGVS<br>(SEQ ID NO: 4) | ASIWWNGNT<br>YNNPSLKS<br>(SEQ ID NO: 6) | TEIIRGRNYYVMDA<br>(SEQ ID NO: 7) |
| 3E11A5-E10<br>3E11A5-G6 | GFSLSTYGMGVS<br>(SEQ ID NO: 5) | | TLITITPFYYVMDA<br>(SEQ ID NO: 8) |
| 5B12D2-B3<br>5B12D2-A4 | | | TLITIAAISHYYVMDA<br>(SEQ ID NO: 9) |

CDRs 1 to 3 may contain, in addition to the above-mentioned amino acid sequence of SEQ ID NOs: 1 to 9, the same amino acid sequence as the amino acid sequence of SEQ ID NOs: 1 to 9 except that one or several amino acids are conservatively substituted. Here, "an amino acid is conservatively substituted" means that a certain amino acid is substituted to an amino acid that exhibits properties similar to the amino acid. It is known in the art that a protein comprising the amino acid sequence that contains the same sequence as a particular amino acid sequence except that one or several amino acids are conservatively substituted has activities equivalent to those of a protein comprising the particular amino acid sequence. In the present disclosure, as long as a monoclonal antibody having such an amino acid sequence in which an amino acid is conservatively substituted and a fragment comprising an antigen-binding region thereof retains an ability to bind to KIR2DS1, such a monoclonal antibody may be included in the monoclonal antibody according to the present disclosure. For example, neutral (polar) amino acids (Asn, Ser, Gln, Thr, Tyr, Cys), neutral (non-polar, that is, hydrophobic) amino acids (Gly, Trp, Met, Pro, Phe, Ala, Val, Leu, Ile), acidic (polar) amino acids (Asp, Glu), basic (polar) amino acid (Arg, His, Lys) may be substituted to an amino acid having the same properties.

Next, a method for preparing the monoclonal antibody according to the present disclosure will be described.

A recombinant KIR2DS1 protein expressed in *Escherichia coli* can for example be purified to be used as an immunogen. As a method of expressing KIR2DS1, an expression method by a recombinant protein expression system using yeast or a cell line (such as human cultured cells (such as HEK cells), or insect cells) or an expression method comprising preparing a BmNPV virus gene in *Escherichia coli* and injecting the resultant directly into an individual silkworm can also be used.

In the preparation of the immunogen, one prepared by adding an adjuvant to the KIR2DS1 protein for the purpose of carrying out effective immunization may be used. Examples of the adjuvant that can be utilized include Freund's complete adjuvant (FCA) and Freund's incomplete adjuvant (FIA).

The immunogen prepared as described above is administered to a mammal, for example, a rat, a mouse, a rabbit, or the like. Immunization is carried out by, for example, subcutaneous (in buttocks or the like), intraperitoneal, foot-pad, intravenous injection. As for the number of immunization, the immunization may be carried out as a single does or may be approximately twice to five times at an interval of several days to several weeks. Antibody producing cells are harvested from the lymph node, the spleen, the peripheral blood, or the like 3 to 20 days after the day of final immunization.

Subsequently, the antibody producing cells are subjected to cell fusion with myeloma cells to obtain a hybridoma. As the myeloma cell, commonly-available established cell line can be used; and preferred is cells with drug selectivity, that is, those having properties, for example, of being incapable of surviving in a HAT selection medium (which contains hypoxanthine, aminopterin, and thymidine) in an unfused state and capable of surviving only in a state of fusion with the antibody producing cell. For examples, mouse myeloma cells (X63/Ag8-653) can be used as the myeloma cell.

The antibody producing cell and the myeloma cell are mixed in a medium without blood serum (for example, RPMI 1640 medium or the like) and undergo cell fusion in the presence of a cell fusion accelerator (for example, polyethylene glycol or the like). It is to be noted that a cell fusion device utilizing electroporation may be used in the cell fusion.

After the cell fusion, an intended hybridoma is selected. For example, a cell suspension prepared by dilution in the HAT selection medium containing inactivated FBS is seeded in a microtiter plate and cultured with the medium being changed as appropriate. After that, cells that develop 10 to 20 days after the beginning of the culturing can be obtained as the hybridoma.

Screening is carried out for the supernatant of the hybridoma culture obtained as described above in order to check the presence of an antibody that binds to KIR2DS1. A known method can be employed as a screening method. For example, enzyme-linked immunosorbent assay (ELISA), enzyme immunoassay (EIA), radioimmunoassay (RIA), or the like can be used; and ELISA can suitably be employed. Cloning of the fusion cell is carried out by a limiting dilution method or the like to establish a hybridoma that produces an intended monoclonal antibody.

Examples of a method of harvesting a monoclonal antibody from an established hybridoma include a method comprising culturing a hybridoma using a Hybridoma-SFM medium to obtain a monoclonal antibody from the culture supernatant. Purification of the antibody is carried out as needed; and a known method such as, for example, affinity chromatography, an ammonium sulfate precipitation method, ion exchange chromatography, or gel filtration chromatography or a combination thereof can be used.

Next, cells that produce the monoclonal antibody according to the present disclosure will be described.

The hybridoma obtained according to the above-mentioned method of preparing a monoclonal antibody can for example be suitably employed as a cell that produces the monoclonal antibody according to the present disclosure.

The present inventors established three kinds of hybridoma, namely 1C7_KIR2DS1, 3E11A5_KIR2DS1, and 5B12D2_KIR2DS1 as the hybridoma producing the monoclonal antibody to KIR2DS1. Each of these hybridomas has been deposited with Incorporated Administrative Agency National Institute of Technology and Evaluation (NITE) Patent Microorganisms Depositary (NPMD) (2-5-8

Kazusakamatari, Kisarazu-shi, Chiba 292-0818, Japan) as of May 9, 2014 (date of deposition), thereafter transferred to International Deposit under the Budapest Treaty (the transfer request was received on Jul. 8, 2015), and given Accession No. NITE BP-01853, Accession No. NITE BP-01855, and Accession No. NITE BP-01854, respectively (the Receipt of a Deposit was issued on Jul. 29, 2015).

The hybridoma 1C7_KIR2DS1 produces 1C7B8-G3, 1C7H12-B1, 1C7B8-E1, and 1C7H12-E4 as clones; hybridoma 3E11A5_KIR2DS1 does 3E11A5-E10 and 3E11A5-G6 as clones; and hybridoma 5B12D2_KIR2DS1 does 5B12D2-B3 and 5B12D2-A4 as clones. It is to be noted that these clones have the amino acid sequence of CDRs 1 to 3 of VL and CDRs 1 to 3 of VH as shown in Table 1 described above.

Further, Table 2 shows SEQ ID numbers corresponding to the base sequence of nucleic acids encoding VL CDRs 1 to 3 and VH CDRs 1 to 3 of the above-mentioned clone.

TABLE 2

| | VL | | |
|---|---|---|---|
| | CDR1 | CDR2 | CDR3 |
| 1C7B8-G3 | aaggccagt | aaggcatccaa | atgcagtctaac |
| 1C7H12-B1 | cagaatgtg | ccggtacact | accaatccgctc |
| 1C7B8-E1 | ggttctaat | (SEQ ID NO: 11) | (SEQ ID NO: 12) |
| 1C7H12-E4 | gtagac | | |
| 3E11A5-E10 | (SEQ ID NO: 10) | | |
| 3E11A5-G6 | | | |
| 5B12D2-B3 | | | |
| 5B12D2-A4 | | | |

| | VH | | |
|---|---|---|---|
| | CDR1 | CDR2 | CDR3 |
| 1C7B8-G3 | ggatttca | gcaagcatttg | acggaaataatt |
| 1C7H12-B1 | ctgagcact | gtggaatggta | cggggtaggaat |
| 1C7B8-E1 | tatagtatg | atacatacaac | tactatgttatg |
| 1C7H12-E4 | ggtgtgagc | aacccatctct | gatgcc |
| | (SEQ ID NO: 13) | gaagagc (SEQ ID NO: 15) | (SEQ ID NO: 16) |
| 3E11A5-E10 | ggatttca | | accctcattact |
| 3E11A5-G6 | ctgagcact | | ataacaccttt |
| 5B12D2-B3 | tatggtatg | | tactatgttatg |
| 5B12D2-A4 | ggtgtgagc (SEQ ID NO: 14) | | gatgcc (SEQ ID NO: 17) actcttattact atagcagctata tcccattactat gttatggatgcc (SEQ ID NO: 18) |

Next, a chimeric antibody and a humanized antibody of the monoclonal antibody of the present disclosure will be described.

A chimeric antibody can be prepared, for example, by introducing a gene of the rat monoclonal antibody produced by the above-mentioned hybridoma into a gene of an antibody molecule derived from another mammal. A method described in Takeda et al., 1985, Nature, 314:452-454; Morrison et al., 1984, Proc. Natl. Acad. Sci., 81:6851-6855; Neuberger et al., 1984, Nature, 312:604-608 can for example be employed as a method of preparing the chimeric antibody. Examples of the chimeric antibody can include a human chimeric antibody that has an amino acid sequence of the variable region of VL and/or VH of the above-mentioned rat monoclonal antibody, for example, containing SEQ ID NOs: 1 to 3 as CDRs 1 to 3 of the VL of the above-mentioned rat monoclonal antibody, respectively and SEQ ID NO: 4, SEQ ID NO: 6, and SEQ ID NO: 7 as CDRs 1 to 3 of VH, respectively, and the human immunoglobulin constant region; a human chimeric antibody that has an amino acid sequence containing SEQ ID NOs: 1 to 3 as CDRs 1 to 3 of the VL of the above-mentioned rat monoclonal antibody, respectively and SEQ ID NO: 4, SEQ ID NO: 6, and SEQ ID NO: 8 as CDRs 1 to 3 of the VH, respectively, and the human immunoglobulin constant region; a human chimeric antibody that has an amino acid sequence containing SEQ ID NOs: 1 to 3 as CDRs 1 to 3 of the VL of the above-mentioned rat monoclonal antibody, respectively and SEQ ID NO: 4, SEQ ID NO: 6, and SEQ ID NO: 9 as CDRs 1 to 3 of the VH, respectively, and the human immunoglobulin constant region; a human chimeric antibody that has an amino acid sequence containing SEQ ID NOs: 1 to 3 as CDRs 1 to 3 of the VL of the above-mentioned rat monoclonal antibody, respectively and SEQ ID NO: 5, SEQ ID NO: 6, and SEQ ID NO: 7 as CDRs 1 to 3 of the VH, respectively, and the human immunoglobulin constant region; a human chimeric antibody that has an amino acid sequence containing SEQ ID NOs: 1 to 3 as CDRs 1 to 3 of the VL of the above-mentioned rat monoclonal antibody, respectively and SEQ ID NO: 5, SEQ ID NO: 6, and SEQ ID NO: 8 as CDRs 1 to 3 of the VH, respectively, and the human immunoglobulin constant region; or a human chimeric antibody that has an amino acid sequence containing SEQ ID NOs: 1 to 3 as CDRs 1 to 3 of the VL of the above-mentioned rat monoclonal antibody, respectively and SEQ ID NO: 5, SEQ ID NO: 6, and SEQ ID NO: 9 as CDRs 1 to 3 of the VH, respectively, and the human immunoglobulin constant region. Any method can be used as appropriate as long as the method is a production method of a chimeric antibody that exerts effects of the present disclosure.

A humanized antibody is an antibody that has for example part of the variable region containing the variable region or the hypervariable region derived from rat monoclonal antibody and the constant region of a human immunoglobulin or part of the variable region and the constant region of a human immunoglobulin. In the case of the humanized antibody, an antibody region part derived from rat preferably accounts for less than about 10% of the entire humanized antibody. The humanized antibody according to the present disclosure has, for example, an amino acid sequence containing SEQ ID NOs: 1 to 3 as CDRs 1 to 3 of VL of the above-mentioned rat monoclonal antibody, respectively and SEQ ID NO: 4, SEQ ID NO: 6, and SEQ ID NO: 7 as CDRs 1 to 3 of VH of the above-mentioned rat monoclonal antibody, respectively; an amino acid sequence containing SEQ ID NOs: 1 to 3 as CDRs 1 to 3 of VL of the above-mentioned rat monoclonal antibody, respectively and SEQ ID NO: 4, SEQ ID NO: 6, and SEQ ID NO: 8 as CDRs 1 to 3 of VH of the above-mentioned rat monoclonal antibody, respectively; an amino acid sequence containing SEQ ID NOs: 1 to 3 as CDRs 1 to 3 of VL of the above-mentioned rat monoclonal antibody, respectively and SEQ ID NO: 4, SEQ ID NO: 6, and SEQ ID NO: 9 as CDRs 1 to 3 of VH of the above-mentioned rat monoclonal antibody, respectively; an amino acid sequence containing SEQ ID NOs: 1 to 3 as CDRs 1 to 3 of VL of the above-mentioned rat monoclonal antibody, respectively and SEQ ID NO: 5, SEQ ID NO: 6, and SEQ ID NO: 7 as CDRs 1 to 3 of VH of the above-mentioned rat monoclonal antibody, respectively; an amino acid sequence containing SEQ ID NOs: 1 to 3 as CDRs 1 to 3 of VL of the above-mentioned rat monoclonal antibody, respectively and SEQ ID NO: 5, SEQ ID NO: 6, and SEQ ID NO: 8 as CDRs 1 to 3 of VH of the above-mentioned rat monoclonal antibody, respectively; or an amino acid sequence containing SEQ ID NOs: 1 to 3 as CDRs 1 to 3 of VL of the above-mentioned rat monoclonal antibody, respectively and SEQ ID NO: 5, SEQ ID NO: 6, and SEQ ID NO: 9 as CDRs 1 to 3 of VH of the above-mentioned rat monoclonal antibody, respectively. Any method can be used as appropriate as long as the method is a preparation method of a humanized antibody that exerts effects of the present disclosure.

The method of preparing the monoclonal antibody or the fragment comprising an antigen-binding region thereof according to the present disclosure, which method utilizes a genetic engineering technique, will be described.

Examples thereof include the following preparation method. From the hybridoma that has been prepared as described above, mRNA is extracted and cDNA is synthesized. This cDNA is inserted into a vector such as a phage or a plasmid to prepare a cDNA library. A recombinant phage, a recombinant plasmid or the like that has cDNA encoding VH or VL is isolated from such a library using, as a probe, a constant region part or a variable region part of a non-human animal antibody (for example, a murine antibody). The entire base sequence of the VH or the VL of an intended antibody on the recombinant phage or the recombinant plasmid is determined by a known sequencing method; and the entire amino acid sequence of VH or VL is estimated based on the base sequence.

Examples of the base sequence encoding the monoclonal antibody according to the present disclosure, for example, the base sequence of the nucleic acid encoding CDRs 1 to 3 of VL and CDRs 1 to 3 of VH include SEQ ID NOs: 10 to 18 (Table 2).

In addition, a mutant with one or several bases being deleted, substituted, added, or inserted in the nucleic acid comprising the base sequence encoding VH or VL, the mutant comprising the base sequence encoding a protein that binds to KIR2DS1 can be used. Here, the term "one or several" refers to 1 to 20, preferably 1 to 15, and more preferably 1 to 10. It is to be noted that the mutant in this case may include a naturally occurring mutant and an artificial mutant.

Further, a mutant comprising a base sequence that hybridizes with a sequence complementary to the base sequence encoding VH or VL in stringent conditions and encodes a protein that binds to KIR2DS1 can also be used. Here, the phrase "stringent conditions" includes, without limitation, for example, hybridization at 30° C. to 50° C., in 3 to 4×SSC (150 mM sodium chloride, 15 mM sodium citrate, pH 7.2) and 0.1 to 0.5% SDS for 1 to 24 hours, more preferably hybridization at 40° C. to 45° C. in 3.4×SSC and 0.3% SDS for 1 to 24 hours, and subsequent washing. Examples of washing conditions include a condition of consecutive washing with a solution containing 2×SSC and 0.1% SDS, 1×SSC solution, and 0.2×SSC solution at room temperature. Note that the combination in the above-mentioned condition is an example and those skilled in the art will be able to achieve the same stringency as described above by combining as appropriate the above condition or other factors (for example, the concentration, length, and GC content of hybridization probe, reaction time of hybridization, or the like) which determine the stringency of hybridization.

The monoclonal antibody according to the present disclosure can be prepared by using an expression vector containing a nucleic acid with the base sequence encoding the VH or the VL of the monoclonal antibody according to the present disclosure or a mutant thereof.

First, the nucleic acid with the base sequence encoding the VH or the VL of the monoclonal antibody or the mutant thereof according to the present disclosure is, for example, subjected to cloning to be incorporated into an expression vector. For example, pAGE107 (Cytotechnology, 3, 133 (1990)), pAGE103 (J. Biochem., 101, 1307 (1987)), pQCxID (Clontech), pQCxIH (Clontech), or the like can be used as the expression vector. Further, in addition to the nucleic acid with the base sequence encoding the VH or the VL or the mutant thereof, a known promoter, a known enhancer, or a known selection marker gene (such as a neomycin-resistance gene or an ampicillin-resistant gene) may be inserted into the expression vector.

Subsequently, the expression vector that has constructed as described above is introduced into host cells to obtain a transformant. As for the host cell used, any can be used without particular limitation as long as the cell is capable of expressing a nucleic acid in the introduced expression vector and producing the monoclonal antibody or the fragment comprising an antigen-binding region thereof according to the present disclosure; and for example, bacteria (such as *Escherichia coli*), yeast (such as *Saccharomyces cerevisiae*), animal cells (such as COS cells or CHO cells), insect cells (such as silkworm, Sf9 cells, or Sf21 cells) can be used. Further, with regard to a method of introducing the vector into the host cell, any method can be employed without particular limitation as long as the method is a known introduction method. Examples of the method of introducing the vector into bacteria or yeast include an electroporation method, a spheroplast method, and a lithium acetate method; and examples of introducing the vector into animal cells or insect cells include an electroporation method, a calcium phosphate method, and a lipofection method.

The transformant is selected, for example, by taking advantage of properties of a marker gene that has been constructed in a nucleic acid to be introduced. In the case of using a neomycin resistance gene, for example, cells exhibiting resistance to G418 agent are selected.

The monoclonal antibody according to the present disclosure can be collected and thereby obtained from a culture prepared by culturing the above-mentioned transformant in a medium. In the present specification, the term "culture" refers to a culture supernatant, a cultured cell, cell homogenate, or the like.

As a method of culturing the transformant, a common method used for culturing host cells may be employed. Either a natural medium or a synthesis medium may be used as a medium as long as the medium is, in the case of culturing the transformant obtained by using bacteria or yeast as the host cell, a medium that contains a carbon source, a nitrogen source, an inorganic salt, or the like and in which the culturing of transformant can be carried out in an efficient fashion. The culturing is usually carried out under aerobic conditions such as culturing with shaking or culturing with aeration and agitation at about 20 to 40° C. approximately for 1 to 24 hours. During the period of culturing, the pH is maintained around at a neutral pH. During the culturing, an antibiotic such as ampicillin or tetracycline may be added to the medium as needed. As for a medium in which the transformant obtained by using animal cells as a host is cultured, a medium prepared by adding fetal bovine serum or the like to a commonly-used medium such as RPMI 1640 medium or D-MEM medium. The culturing is usually carried out in the presence of 5% $CO_2$ at about 37° C. approximately for one to seven days.

During the culturing, an antibiotic such as streptomycin or penicillin may be added to the medium as needed.

After the culturing, the monoclonal antibody according to the present disclosure is collected from the culture. For example, in cases where the antibody is produced inside cells or bacterial cells, a protein is extracted from a homogenate of the cell or the bacterial cell by a known method and the antibody is thereby collected. Further, in cases where the antibody is for example produced outside of cells or bacterial cells, the antibody is collected by a known method directly from a culture liquid or from a culture liquid after removing the cell or the bacterial cell by centrifugation or the like. The monoclonal antibody according to the present disclosure collected from the culture may be purified by a known method as needed.

The activity of the thus obtained monoclonal antibody according to the present disclosure to bind to KIR2DS1 can be checked by the above-mentioned method.

Next, actions of the pharmaceutical composition according to the present disclosure and the monoclonal antibody according to the present disclosure on KIR2DS1 will be described.

The pharmaceutical composition according to the present disclosure contains the monoclonal antibody according to the present disclosure which binds specifically to KIR2DS1. Therefore, when the pharmaceutical composition according to the present disclosure is administered to a subject, the monoclonal antibody according to the present disclosure bonds to KIR2DS1 which is present on the cell surface of NK cells in the body of the subject and can act as an agonist for or antagonist against KIR2DS1 depending on circumstances.

It is to be noted that, the monoclonal antibody according to the present disclosure that acts as an agonist for KIR2DS1 may be subjected to conversion via fragmentation treatment by a known method to generate a fragment such as Fab, Fab', F(ab')2, or a single chain antibody (scFv) or to cross-linking treatment so as to act as an antagonist against KIR2DS1. Further, conversely to this, the monoclonal antibody according to the present disclosure that acts as an antagonist against KIR2DS1 may be subjected to conversion via the same treatment as described above so as to act as an agonist for KIR2DS1.

In cases where the monoclonal antibody according to the present disclosure acts as an agonist for KIR2DS1, the antibody activates KIR2DS1 to activate NK cells and thus can be used as an immunostimulating agent (an NK cell activator), an anti-cancer agent, or the like.

In the case of using as the immunostimulating agent, what is expected are effects of treating and/or preventing, for example, acquired immune deficiency syndrome (AIDS) by human immunodeficiency virus infection (for example, opportunistic infection such as candida esophagitis, Pneumocystis pneumonia, toxoplasmosis, tuberculosis, *Mycobacterium avium* complex infection, cryptosporidiosis, cryptococcal meningitis, cytomegalovirus infection, progressive multifocal leukoencephalopathy, or the like), immunodeficiency diseases including immunodeficiency, primary immunodeficiency syndrome, and the like associated with severe diseases (for example, cancer, aplastic anemia, leukemia, myelofibrosis, renal failure, diabetes, liver disease, or splenic disease).

In the case of using as the anti-cancer agent, what is expected are effects of treating and/or preventing chronic myelogenous leukemia (CML), chronic lymphocytic leukemia (CLL), adrenocortical cancer, anal cancer, biliary canal cancer, bladder cancer, breast cancer, cervical cancer, colon cancer, endometrial cancer, esophageal cancer, Ewing's cancer, gall bladder cancer, Hodgkin's disease, hypopharyngeal cancer, laryngeal cancer, lip and oral cancer, liver cancer, lung cancer—non-small cell, lymphoma—non-Hodgkin's, melanoma, mesothelioma, multiple myeloma, ovarian cancer, pancreatic cancer, prostate cancer, stomach cancer, testicular cancer, thyroid cancer, or the like.

In cases where the monoclonal antibody according to the present disclosure acts as an antagonist against KIR2DS1, the antibody inactivates KIR2DS1 to inactivate NK cells and thus can be used as a therapeutic agent for autoimmune disease, an immunosuppressant after transplant, or the like (an NK cell inactivator).

Examples of the autoimmune disease include arthritis, autoimmune hepatitis, autoimmune glomerulonephritis, autoimmune insulitis, autoimmune orchitis, autoimmune oophoritis, ulcerative colitis, Sjogren's syndrome, Crohn's disease, Behcet's disease, Wegener's granulomatosis, hypersensitivity vasculitis, periarteritis nodosa, Hashimoto's thyroiditis, myxedema, Graves' disease, Addison's disease, autoimmune hemolytic anemia, idiopathic thrombocythemia, pernicious anemia, myasthenia gravis, demyelinating disease, aortitis syndrome, psoriasis, pemphigus, pemphigoid, connective tissue diseases (for example, systemic lupus erythematosus, chronic rheumatoid arthritis, diffuse systemic sclerosis, progressive systemic sclerosis, dermatomyositis, polyarteritis nodosa, rheumatic fever, and the like), Guillain-Barre syndrome, type II polyendocrine autoimmune syndrome, primary biliary liver cirrhosis, vitiligo vulgaris, and type 1 diabetes mellitus; and effects of treating and/or preventing these diseases are expected.

Examples of the immunosuppressant after transplant include rejection after kidney transplant, liver transplant, heart transplant, or lung transplant, rejection in bone marrow transplant, and graft versus host disease; and effects of treating and/or preventing these are expected.

[The monoclonal antibody according to the present disclosure specifically binds to KIR2DS1 and does not cross-react with other KIRs (KIR2DL1, KIR2DS2, KIR2DL2, and KIR2DL3); and more specific effects of treatment and/or prevention can be expected.

An administration route of the pharmaceutical composition according to the present disclosure may be selected as appropriate from oral administration, intravenous administration, intraperitoneal administration, intradermal administration, subcutaneous administration, buccal administration, sublingual administration, intratracheal administration, intrarectal administration, intramuscular administration, and the like. The dosage form of this pharmaceutical composition may also be freely selected; and the composition can be prepared as appropriate into an oral solid formulation such as a tablet, a granule, a powder, or a capsule; an oral liquid formulation such as an oral liquid medicine or a syrup; a parenteral liquid formulation such as an injection solution; in addition, a spray, a suppository, an ointment, and a tape.

The pharmaceutical composition according to the present disclosure is allowed to contain as appropriate an excipient, a binder, a disintegrant, a thickener, a dispersant, a reabsorption accelerator, a taste masking agent, a buffering agent, a surfactant, a solubilization auxiliary agent, a preservative, emulsifier, an isotonic agent, a stabilizers, a pH adjusting agent, or the like, each of which is commonly used.

The dose of the pharmaceutical composition according to the present disclosure may be selected as appropriate depending on a disease to be applied, dosage form, patient's age and body weight, and the like.

When the pharmaceutical composition according to the present disclosure is administered to a subject, whether or not the subject has KIR2DS1 may be examined, prior to the administration, by using the monoclonal antibody of the present disclosure. This is because about half of Japanese people have KIR2DS1 and therapeutic and/or prophylactic effects can be expected from administration of such a pharmaceutical composition to a subject with KIR2DS1. As just described above, the monoclonal antibody of the present disclosure may also be used for companion diagnostics.

Next, a method of detecting KIR2DS1 in a sample for the purpose of examining whether or not a subject has KIR2DS1 will be described.

A method of detecting KIR2DS1 in a sample comprises:
(a) a step of bringing the monoclonal antibody of the present disclosure into contact with a sample from a subject; and
(b) a step of determining whether or not the monoclonal antibody of the present disclosure binds to KIR2DS1 in the sample from the subject.

Examples of the above-mentioned "sample" derived from a subject include a tissue or cell sample (a tissue or a cell from cancer of the stomach, the duodenum, the large intestine, the pancreas, the gall bladder, the bile duct, the bronchi, the lung, or the like), and a biological fluid sample (such as gastric mucus, duodenal juice, pancreatic juice, bile, ascites, sputum, bronchoalveolar lavage fluid, blood, blood serum, blood plasma, and the like). In the case of immunostaining, for example, a tissue sample (biopsy specimen, resected specimen) or a cytological diagnosis sample can be used.

The term "contact" in the above-mentioned step (a) means that the monoclonal antibody of the present disclosure is allowed to be in proximity to KIR2DS1 in a sample so as to be able to bind to KIR2DS1; and the contact can be accomplished by, for example, mixing a solution that contains the sample with a solution that contains the monoclonal antibody according to the present disclosure, immersing a solid that contains the sample in a solution that contains the monoclonal antibody according to the present disclosure, immersing one prepared by immobilizing the antibody according to the present disclosure on a solid phase support (such as, for example, a membrane or a bead) in a solution that contains the sample, or the like.

In the above-mentioned step (b), whether or not the monoclonal antibody of the present disclosure binds to KIR2DS1 in the sample from the subject can be determined by using immunohistochemical staining and immunoelectron microscopy, as well as an immunoassay including ELISA, EIA, fluorescence immunoassay, radioimmunoassay (RIA), immunochromatography, and western blotting.

In the case of the immunohistochemical staining or the immunoelectron microscopy, the detection can be carried out in situ. In that case, a histological sample (a biopsy tissue sample, a tissue section embedded in paraffin, or the like) is collected from the subject; and a labeled monoclonal antibody of the present disclosure can be brought into contact with such a histological sample.

The immunoassay may be carried out either in a liquid phase system or a solid phase system. In addition, the format of immunoassay is not restricted and may be a sandwich method, a competitive method, or the like, in addition to a direct solid phase method. A complex of KIR2DS1 and the antibody may be separated by known separation means (chromatography, a salting out method, an alcohol crystallization method, an enzymatic method, a solid phase method, or the like) such that the signal of the label is detected. For example, in cases where a solid phase system is used as an example of the immunoassay, an antibody or an antigen-binding fragment may be immobilized on a solid phase support or carrier (a resin plate, a membrane, a bead, or the like) or a sample may be subjected to immobilization. The antibody or the antigen-binding fragment is, for example, immobilized on the solid phase support; and the support is washed with an appropriate buffer and then treated with the sample. Subsequently, the solid phase support is subjected to the second wash with the buffer to remove an unbound antibody or an unbound antigen-binding fragment. The bound antibody or the bound antigen-binding fragment on the solid support is then detected by routine means, thereby allowing for detection of the binding of KIR2DS1 in the sample with the antibody or the antigen-binding fragment. The bound antibody or the bound antigen-binding fragment on the solid sample can also be detected by routine means after the solid sample is treated with a solution containing an antibody or an antigen-binding fragment and subsequently washed with a buffer to remove an unbound antibody or an unbound antigen-binding fragment.

With regard to the detection of the binding of the antibody according to the present disclosure with KIR2DS1 in a sample, in order to facilitate the detection, the antibody may be labeled to be indirectly detected. In the case of the enzyme immunoassay, peroxidase, β-galactosidase, alkaline phosphatase, glucose oxidase, acetylcholinesterase, lactate dehydrogenase, amylase, or the like, or an enzyme inhibitor, a coenzyme, or the like, can for example be bound to the antibody by a known method for the detection. In the case of the fluorescence immunoassay, fluorescein isothiocyanate (FITC), tetramethylrhodamine isothiocyanate (TRITC), or the like can for example be bound to the antibody by a known method for the detection. In the case of the radioimmunoassay, tritium, iodine 125, iodine 131, or the like can for example be bound to the antibody by a known method for the detection.

Further, for example, in cases where the binding of the antibody according to the present disclosure with KIR2DS1 in a sample using a labeled secondary antibody is detected, the antibody or the antigen-binding fragment of the present disclosure is brought into reaction with the sample (primary reaction) and the obtained complex is brought into reaction with the labeled secondary antibody (secondary reaction). The primary reaction and the secondary reaction may be carried out in reverse order, may be carried out at the same time, or may be carried out at different times. By the primary reaction and the secondary reaction, a complex of KIR2DS1—the antibody of the present disclosure—the labeled secondary antibody or a complex of the antibody of the present disclosure-KIR2DS1—the labeled secondary antibody is formed. Then, in cases where quantification is carried out, an unbound labeled secondary antibody is separated and then the amount of KIR2DS1 in the sample can be measured from the amount of bound labeled secondary antibody or the amount of unbound labeled secondary antibody.

In cases where a biotin-avidin complex system is used to detect the binding of the antibody according to the present disclosure with KIR2DS1 in the sample is, the sample is brought into reaction with a biotinylated antibody and then the obtained complex is brought into reaction with an avidin that has been added with a label. Because avidin is capable of specifically binding with biotin, the binding of the antibody with KIR2DS1 can be measured by detecting the signal of the label added to the avidin. The label added to avidin is not particularly restricted; and preferred is, for example, an enzyme label (peroxidase, alkaline phosphatase, or the like).

The detection of the signal of the label can also be carried out according to a known method in the art. In cases where the enzyme label is used, for example, a substrate that develops colors when broken down by an action of the enzyme is added and the amount of substrate broken down is optically measured to determine enzymatic activity. This is converted into the amount of antibody bound which is compared to a standard value to thereby calculate the amount of antibody. The substrate varies depending on the kind of enzyme used. When peroxidase is used as the enzyme, 3,3',5,5'-tetramethylbenzidine (TMB), diaminobenzidine (DAB), or the like can be used; and when alkaline phosphatase is used as the enzyme, paranitrophenol or the like can be used. A fluorescent label can be detected and quantified using, for example, a fluorescence microscope, a plate reader, or the like. In cases where a radioisotope label is used, the level of radiation emitted by the radioisotope label is measured by a scintillation counter or the like.

Next, a method for measuring the population of KIR2DS1 and KIR2DL1 in a sample will be described.

KIR2DS1 and KIR2DL1 share a high sequence homology in the extracellular domain and are believed to recognize the same ligand. Because of this, no antibodies that specifically bind to KIR2DS1 have been conventionally found; and it has thus been impossible to accurately quantify a population of KIR2DS1 and KIR2DL1 in a sample. Use of the monoclonal antibody according to the present disclosure which specifically binds to KIR2DS1 enables the population of KIR2DS1 and KIR2DL1 in the sample to be accurately measured, which makes it possible to, for example, reveal a relation between the onset of disease and an expression level ratio of KIR2DS1/KIR2DL1. The use is expected to be applied to diagnosis of a particular disease.

The method for measuring a population of KIR2DS1 and KIR2DL1 in a sample comprises:

a step of bringing a sample from a subject into contact with the monoclonal antibody according to the present disclosure to measure the amount of KIR2DS1 in the sample; and a step of measuring the amount of KIR2DL1 in the sample.

The above-mentioned terms "sample from a subject" and "contact" have the same meaning as described above; and the peripheral blood can preferably be employed as the sample from a subject. Further, the amount of KIR2DL1 in a sample can be measured by bringing the sample into contact with, for example, an anti-KIR2DL1 antibody [2F9] (Abcam) and using, in the same manner as described above, immunohistochemical staining and immunoelectron microscopy, as well as an immunoassay including ELISA, EIA, fluorescence immunoassay, radioimmunoassay (RIA), immunochromatography, and western blotting. As just described above, the individual measurement of the amount of KIR2DS1 and the amount of KIR2DL1 in the sample allows for accurate quantification of the population of KIR2DS1 and KIR2DL1.

Next, an monoclonal antibody that neither act as an agonist for KIR2DS1 nor act as an antagonist against KIR2DS1 will be described.

The monoclonal antibody according to the present disclosure, depending on circumstances, neither act as an agonist for KIR2DS1 nor act as an antagonist against KIR2DS1, that is, may transduce no signals for KIR2DS1. In this case, this antibody may be subjected to conversion so as to act as an agonist for or an antagonist against KIR2DS1 by fragmentation treatment to generate a fragment such as Fab, Fab', F(ab')2, or a single chain antibody (scFv) or cross-linking treatment. Further, conversely to this, the antibody according to the present disclosure that acts as an agonist for or an antagonist against KIR2DS1 may be subjected to the same treatment as described above to be converted to the antibody that transduces no signals.

Further, a substance that binds to KIR2DL1 can be screened by using such an antibody that transduces no signals for KIR2DS1. This screening method comprises:

(A) a step of administering the monoclonal antibody according to the present disclosure to cell population;

(B) a step of measuring the level A of KIR2DL1 activity in the cell population;

(C) a step of administering a candidate substance to the cell population;

(D) a step of measuring the level B of KIR2DL1 activity in the cell population after the administration of the candidate substance to the cell population; and (E) a step of comparing the level A with the level B.

The above-mentioned phrase "administer to cell population" includes, for example, administering (the monoclonal antibody according to the present disclosure or a candidate substance) to a transgenic animal (a mouse, a rat, a rabbit, or the like) that expresses KIR2DS1 and KIR2DL1 and adding (the monoclonal antibody according to the present disclosure or a candidate substance) to cultured cells that express KIR2DS1 and KIR2DL1. Further, the above-mentioned terms "candidate substance" and "substance" include a compound, an antibody, a protein, a peptide, and the like. It is to be noted that the level of KIR2DL1 activity can be measured by, for example, evaluating phosphorylation of a KIR2DL1 intracellular motif. The evaluation of the phosphorylation is feasible by, for example, detecting KIR2DL1 phosphorylation by Western blotting with an anti-phosphorylated tyrosine antibody. Further, a capability of inhibiting activities by KIR2DL1 can also be evaluated by, for example, measuring KIR2DL1-expressing NK cell's cytotoxicity against target cells.

If the monoclonal antibody according to the present disclosure is in advance administered to cell population, screening can be carried out for a substance that specifically binds to KIR2DL1 because the monoclonal antibody according to the present disclosure specifically binds to KIR2DS1. It is to be noted that if the level B of KIR2DL1 activity after the administration of a candidate substance is larger than the level A of KIR2DL1 activity before the administration of a candidate substance, such a candidate substance is an agonist for KIR2DL1. On the other hand, if the level B of KIR2DL1 activity after the administration of a candidate substance is smaller than the level A of KIR2DL1 activity before the administration of a candidate substance, such a candidate substance is an antagonist against KIR2DL1.

EXAMPLES

By way of the following examples, the present disclosure will now be specifically described; but the present disclosure is not limited to these examples.

Example 1

A monoclonal antibody capable of specifically binding with KIR2DS1, one of NK cell-activating receptors was prepared as follows.

1. Preparation of Antigen Protein

A recombinant KIR2DS1 expressed in *Escherichia coli* was used as an antigen protein.

A modified pGMT7 vector was treated with NdeI and HindIII; and the extracellular domain of KIR2DS1 (base sequence: SEQ ID NO: 19, amino acid sequence: SEQ ID NO: 20) was introduced therein. *Escherichia coli* (BL21 (DE3)pLysS) was transformed with this plasmid containing the extracellular domain of KIR2DS1 and allowed to form colonies on an agar plate containing ampicillin. One colony was picked and cultured with shaking in a culture medium containing ampicillin. At the logarithmic growth phase, isopropyl-β-thiogalactopyranoside (IPTG) was added thereto so as to be 1 mM in concentration to thereby induce the expression of a recombinant protein. *Escherichia coli* cells were collected by centrifugation and suspended in a resuspension buffer (50 mM Tris-HCl pH 8.0, 100 mM NaCl). The resulting suspension was sonicated and then washed with a Triton washing buffer (50 mM Tris-HCl pH 8.0, 100 mM NaCl, 0.5% Triton X-100). The resultant was solublized by using a guanidine solution (6 M GuHCl, 50 mM Tris-HCl pH 8.0, 10 mM EDTA) and then gradually added with a refolding buffer (100 mM Tris-HCl pH 8.0, 400 mM L-arginine hydrochloride, 2 mM EDTA, 3.73 mM Cystamine, 6.73 mM Cystamine) to allow refolding. The resultant was concentrated using a cross flow filtration system (Vivaflow MW 10,000) and then concentrated by ultrafiltration (Amicon Ultra MW 10,000). Subsequently, the resulting concentrate was purified using a gel filtration chromatography (AKTA system) (column: Superdex 75), thereby obtaining a protein liquid (antigen). This protein liquid and Adjuvant Complete Freund (Difco Laboratories) were mixed at 1:1 by ultrasonication, which was used as an antigen liquid.

2. Immunization of Rat and Preparation of Iliac Lymph Node Cell Liquid

Four Wister rats (eight weeks of age, female) (Sankyo Labo Service Corporation, Inc.) were provided. For immunization, 250 µg of antigen was injected per rat. To be more specific, 500 µL per rat of 0.5 mg/mL KIR2DS1 protein antigen liquid was injected into rat buttock. Two weeks after the immunization, the blood was drawn by cardiac puncture and the iliac lymph node was at the same time taken out. The harvested iliac lymph node was placed in RPMI 1640 medium (containing L-glutamine and phenol red) (WAKO) in a dish and ground in the above culture medium to yield a cell suspension. The cell suspension was transferred to a tube and left to stand for three minutes. The upper layer was transferred to another tube and centrifuged (1200 rpm for five minutes). Cells were suspended in the RPMI 1640 medium and further centrifuged (1200 rpm for five minutes). Subsequently, cells were suspended in 2 mL of RPMI 1640 medium and used as an iliac lymph node cell liquid ($4 \times 10^7$ iliac lymph node cells were obtained in total).

3. Cell Fusion

The thus obtained $4 \times 10^7$ iliac lymph node cells in the RPMI 1640 medium were mixed with $4 \times 10^6$ mouse myeloma cells (X63/Ag8-653) that had been suspended in 2 mL of RPMI 1640 medium; and the cell mixture solution was transferred to a 50 mL tube and centrifuged (1500 rpm for five minutes). The RPMI medium 1640 was removed and then a precipitate in the tube was broken up well. One milliliter of 50% PEG solution (PEG 1500, Roche Diagnostics) was added thereto and the tube was rotated to mix for one minute. The resultant was gently suspended in 2 mL of RPMI 1640 medium and further gently suspended in 8 mL of RPMI 1640 medium. The cell mixture solution was centrifuged (1000 rpm for 10 minutes). The resulting cells were suspended in 50 mL of GIT-HAT medium (described later) and seeded in five 96-well plates at 100 µmL/well. Those cells were cultured at 37° C. for five days. After five days, each well was added with GIT-HAT medium so as roughly to be filled to about 80% of well's capacity. On the 12th day after the beginning of the culturing, a colony that was able to be confirmed as a single clone in single well was appeared in 233 wells.

It is to be noted that the composition of GIT-HAT medium (400 mL) is as follows:

| | |
|---|---|
| GIT medium (Nihon Pharmaceutical Co., Ltd.) | 332 mL |
| Inactivated FBS (final 10%) | 40 mL |
| BM-condimed H1 (Roche Diagnostics) (final 5%) | 20 mL |
| 50 x HAT (Invitrogen) | 8 mL |

4. Primary Screening

Primary screening was performed by ELISA method using the culture supernatant obtained as described above.

An antigen protein liquid for ELISA for the primary screening was prepared as follows: A KIR2DS1 protein antigen liquid and a KIR2DL1 protein antigen liquid were prepared using *Escherichia coli* strain Origami (DE3) as a competent cell. To be more specific, *Escherichia coli* (Origami (DE3)) was transformed with a plasmid obtained by introducing the extracellular domain of KIR2DS1 (base sequence: SEQ ID NO: 19, amino acid sequence: SEQ ID NO: 20) or the extracellular domain of KIR2DL1 (base sequence: SEQ ID NO: 21, amino acid sequence: SEQ ID NO: 22) into the pGMT7 vector, which was described above, and allowed to form colonies on an agar plate containing ampicillin. One colony was picked and cultured with shaking in the culture medium containing ampicillin. At the logarithmic growth phase, isopropyl-β-thiogalactopyranoside (IPTG) was added thereto so as to be 1 mM in concentration to thereby induce the expression of a recombinant protein.

*Escherichia coli* cells were collected by centrifugation and suspended in a resuspension buffer (50 mM Tris-HCl pH 8.0, 100 mM NaCl). The resulting suspension was sonicated and then washed with a Triton washing buffer (50 mM Tris-HCl pH 8.0, 100 mM NaCl, 0.5% Triton X-100). The resultant was solublized by using a guanidine solution (6 M GuHCl, 50 mM Tris-HCl pH 8.0, 10 mM EDTA) and then gradually added with a refolding buffer (100 mM Tris-HCl pH 8.0, 400 mM L-arginine hydrochloride, 2 mM EDTA, 3.73 mM Cystamine, 6.73 mM Cystamine) to allow refolding. The resultant was concentrated using a cross flow filtration system (Vivaflow MW 10,000) and then concentrated by ultrafiltration (Amicon Ultra MW 10,000). Subsequently, the resulting concentrate was purified using a gel filtration chromatography (AKTA system) (column: Superdex 75), thereby obtaining a protein liquid (KIR2DS1, KIR2DL1). The protein concentration of each antigen liquid was 50 ng/50 µL.

ELISA was carried out as follows. The antigen protein liquid was diluted with a carbonic acid-carbonate buffer ($Na_2CO_3$:$NaHCO_3$=1:1.825), aliquoted into a microtiter plate (96 wells, Nunc Maxisorp) at 50 ng of antigen protein per well, and left to stand at room temperature for two hours. Subsequently, the well was washed with a washing buffer (0.1% Tween 20-PBS(–)) three times, added with 150 µL of a blocking solution (BlockAce (Snow Brand) diluted at 1:4 in 1×PBS(–)), incubated at 37° C. for one hour incubated, and washed three times in the same manner as described above. To each well, 100 µL of the culture supernatant obtained as described above was aliquoted and incubated at 37° C. for one hour. Then, the well was washed three times in the same manner as described above; and 50 μL of secondary antibody solution (one prepared by diluting a secondary antibody (anti-rat IgG-HRP) at 1:5000 in 0.1% Tween 20-PBS(−)) was aliquoted into each well and incubated at 37° C. for one hour. Thereafter, the well was washed three times in the same manner as described above; and 100 μL of ABTS solution (5 mL of citric acid buffer, 1 mg of ABTS (Wako), 3.3 μL of hydrogen peroxide solution) was added to each well and left to stand at room temperature for 5 to 30 minutes. Absorbance (OD 415 nm) was then measured. It is to noted that rat anti-serum No. 2 (×5000, ×2000) (50 μL) was used as a positive control and GIT-HAT medium (50 μL) was as a negative control in ELISA.

As the result of the primary screening, 16 positive clones for the KIR2DS1 protein antigen was obtained from 233 wells.

5. Secondary Screening

Secondary screening was carried out for 16 positive clones that have obtained in the primary screening by the ELISA method.

An antigen protein liquid for ELISA for the secondary screening was prepared as follows.

The KIR2DS1 protein was expressed using *Escherichia coli* strain Origami (DE3) as a competent cell in the same manner as described above.

The KIR2DL1 protein was expressed using the silkworm. To be more specific, a plasmid prepared by introducing the extracellular domain of KIR2DL1 (base sequence: SEQ ID NO: 21, amino acid sequence: SEQ ID NO: 22) into pFastBac vector (a vector that can be used for Tn7 site specific transposition) was subjected to transposition to an in-house developed DH10Bac BmNPV competent cell (one prepared by introducing, BmNPV bacmid which is previously reported in Efficient large-scale protein production of larvae and pupae of silkworm by *Bombyx mori* nuclear polyhedrosis virus bacmid system. Motohashi T, Shimojima T, Fukagawa T, Maenaka K, Park E Y. Biochem Biophys Res Commun. 2005 Jan. 21; 326(3):564-9. into DH10B) and the resultant was cultured in a culture medium containing tetracycline and gentamicin. The resulting culture was then plated onto an agar medium and cultured at 37° C. Colonies were picked; and colony PCR was carried out. A PCR solution was prepared as described below; and Forward primer (5'-gttttcccagtcacgac-3', SEQ ID NO: 23) and Reverse primer (5'-caggaaacagctatgac-3', SEQ ID NO: 24) were used as primers.

| | |
|---|---|
| Go Taq DNA polymerase (Promega Corporation) | 4 μL |
| Forward primer | 1 μL |
| Reverse primer | 1 μL |
| Milli Q | 2 μL |

Conditions for PCR were 95° C. for 5 minutes, 95° C. for 30 seconds—50° C. for 30 seconds—72° C. for 3 minutes 30 seconds×25 cycles, 72° C. for 10 minutes, 4° C.×∞. A positive colony was inoculated in a medium containing kanamycin and gentamicin and cultured at 37° C. overnight. The cultured bacterial cells were collected and the bacmid was purified using Plasmid Midi Kit (QIAGEN). To 1 μg of the purified bacmid (in 50 μL of Milli Q), 3 μL of DMRIE-C (Invitrogen) was added; and the resultant was inoculated into fifth instar silkworm (Ehime Sanshu). Six days after the inoculation, the silkworm was cut open to collect a body fluid and a fat body; and a His-tagged protein was purified using Ni Sepharose 6 Fast Flow (GE Healthcare), thereby obtaining a protein liquid (KIR2DL1). The concentration of the protein in antigen liquid was 50 ng/50 μL.

ELISA was carried out in the same manner as described for the primary screening. Note that anti-rat IgG-HRP was diluted at 1:3000 in 0.1% Tween 20-PBS(−) to be used as a secondary antibody; and rat anti-serum No. 2 (×5000, ×2000, ×1000) (50 μL) was used as a positive control.

As the result of the secondary screening, 11 positive clones for the KIR2DS1 protein antigen were obtained out of 16 clones.

6. Limiting Dilution

The positive clone obtained as described above was scaled up; and limiting dilution was repeated to obtain a single clone.

The limiting dilution was carried out as follows. A culture liquid was prepared at one cell/100 μL; and aliquoted into each well of a 96-well plate at 100 μL. The cell was cultured at 37° C. Once a colony forms, the screening by the ELISA method was carried out for a well with a single clone in the same manner as described for the above secondary screening; and a positive clone was subjected to scale-up. Thereafter, the same limiting dilution as described above was again carried out; and 11×2=22 clones of positive clones for the KIR2DS1 protein antigen were stocked.

7. Purification of Antibody

Each of 22 clones obtained as described above was purified.

The purification of the antibody was carried out as follows. In the case in which a hybridoma that had been cultured (50 mL/75 cm² flask) went through adaptation, 20 mL of culture liquid was added to 30 mL of Hybridoma-SFM medium (GIBCO, Life Technologies Corporation) and cultured at 37° C. until the cell grew. Cells were thereafter collected by centrifugation at 1200 rpm for three minutes and cultured in 40 mL of Hybridoma-SFM medium. On the other hand, in the case in which the hybridoma did not go through adaptation, 50 mL of hybridoma culture medium was centrifuged at 1200 rpm for three minutes to collect cells which were washed with 10 mL of Hybridoma-SFM medium. Cells were collected by another centrifugation and cultured in 40 mL of Hybridoma-SFM medium. After large particles were removed using a syringe type filter (0.45 μm), the culture supernatant was purified by an affinity chromatography using Protein G column Sepharose 4Fast Flow (GE Healthcare) (500 μL).

Example 2

With regard to the monoclonal antibody produced by the hybridomas (22 clones), each of which was obtained as a single clone in Example 1, the binding specificity for KIR family proteins KIR2DS1, KIR2DL1, KIR2DS2, KIR2DL2, and KIR2DL3, which KIR family proteins share a highly homologous extracellular domain, was examined by ELISA and a surface plasmon resonance (SPR) method.

ELISA was carried out three times in the same manner as described above. Note that the primary antibody, the secondary antibody, the detection system, and the like are as follows:

It is to be noted that a protein liquid (antigen) of KIR2DS2, KIR2DL2, or KIR2DL3 was obtained by transforming, in the same manner as described above, *Escherichia coli* (BL21(DE3)pLysS) with a plasmid prepared by introducing the extracellular domain of KIR2DS2 (base sequence: SEQ ID NO: 25, amino acid sequence: SEQ ID NO: 26), the extracellular domain of KIR2DL2 (base sequence: SEQ ID NO: 27, amino acid sequence: SEQ ID NO: 28), or the extracellular domain of KIR2DL3 (base sequence: SEQ ID NO: 29, amino acid sequence: SEQ ID NO: 30) into the same pGMT7 vector as described above.

ELISA-1 and ELISA-2:
Antigen: 50 ng/50 µL (/well)
Primary antibody: Purified antibody (1/100) 50 µL/well
Positive control-1: Rat anti-serum (×1000, 2000, 5000)
Control: Antibody before purification (2B7C2-B3) (a culture supernatant (GIT), flow through at the time of purification)
Negative control: 0.1 M Glycine-HCl (used as an elution buffer when the antibody was purified and had been neutralized)
Secondary antibody: Anti-rat IgG-HRP (×3000) 50 µL/well
Detection system: ABTS (415 nm)
ELISA-3
Antigen: 50 ng/50 µL (/well)
Primary antibody: Purified antibody (undiluted liquid) 50 µL/well
Positive control-1: Rat anti-serum (×1000, 2000, 5000)
Positive control-2: Purified antibody (1C7B8-E1) (×100)
Negative control: 0.1 M Glycine-HCl (used as an elution buffer when the antibody was purified and had been neutralized)
Secondary antibody: Anti-rat IgG-HRP (×3000) 50 µL/well
Detection system: ABTS (415 nm)

SPR was carried out as follows. First, the C terminus of KIR2DS1 and KIR2DL1 was specifically biotinylated (reaction buffer: 50 mM D-biotin, 100 mM ATP, 15 µM BirA); and KIR2DS1 and KIR2DL1 were each separated from biotin left in the reaction buffer by gel filtration chromatography (Superdex 75). For SPR measurement, a surface plasmon resonance experiment for KIRs and the prepared antibody was carried out using Biacore 3000 (GE Healthcare) (measurement conditions: Biotin capture kit CAP chip (GE Healthcare), HBS-EP buffer (10 mM Hepes pH 7.5, 150 mM NaCl, 3.4 mM EDTA, 0.005% Surfactant P20), 25° C.). As for the antibody, one purified from a hybridoma culture supernatant by a protein G column, followed by buffer substitution with HBS-EP (by ultrafiltration) was used. CAP chip was used for a chip; and biotinylated KIR2DS1, biotinylated KIR2DL1, and BSA, which was a negative control, were immobilized on the chip that has been immobilized with SA in the Biotin capture kit. Subsequently, each antibody (35 µL) was dissolved in HBS-EP, which was a running buffer, was flowed at 2 µL/min.

The results were shown in Table 3. In Table 3, "O" indicates that the antibody bound to a corresponding KIR family protein and "X" did not bind to a corresponding KIR family protein. Among 22 clones whose binding specificity was evaluated, eight clones, 1C7B8-G3, 1C7H12-B1, 1C7B8-E1, 1C7H12-E4, 3E11A5-E10, 3E11A5-G6, 5B12D2-B3, and 5B12D2-A4 have been shown not to bind to KIR2DL1, KIR2DS2, KIR2DL2 and KIR2DL3 and to specifically bind only to KIR2DS1.

TABLE 3

| clone | KIR2DS1 | KIR2DL1 | KIR2DS2 | KIR2DL2 | KIR2DL3 |
|---|---|---|---|---|---|
| 1C7B8-G3 | O | X | X | X | X |
| 1C7H12-B1 | O | X | X | X | X |
| 1C7B8-E1 | O | X | X | X | X |
| 1C7H12-E4 | O | X | X | X | X |
| 3E11A5-E10 | O | X | X | X | X |

TABLE 3-continued

| clone | KIR2DS1 | KIR2DL1 | KIR2DS2 | KIR2DL2 | KIR2DL3 |
|---|---|---|---|---|---|
| 3E11A5-G6 | O | X | X | X | X |
| 5B12D2-B3 | O | X | X | X | X |
| 5B12D2-A4 | O | X | X | X | X |

Figure 2:
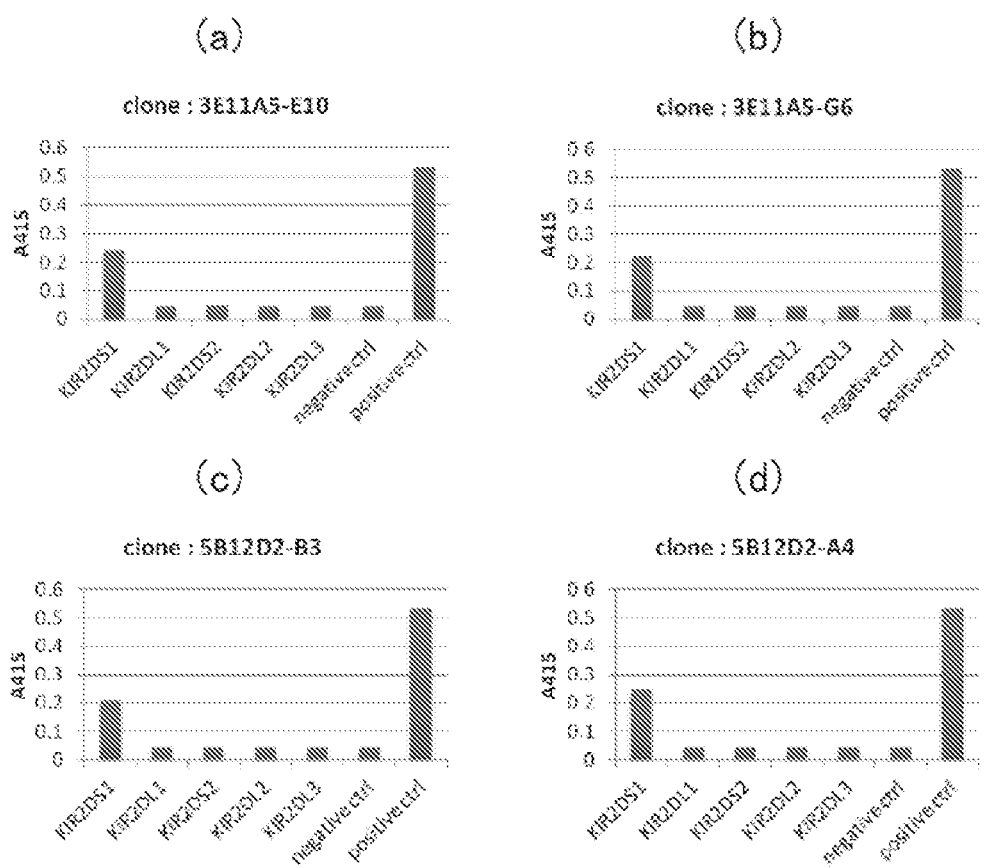
FIG. 2 is a figure showing the results of ELISA.
Figure 3:
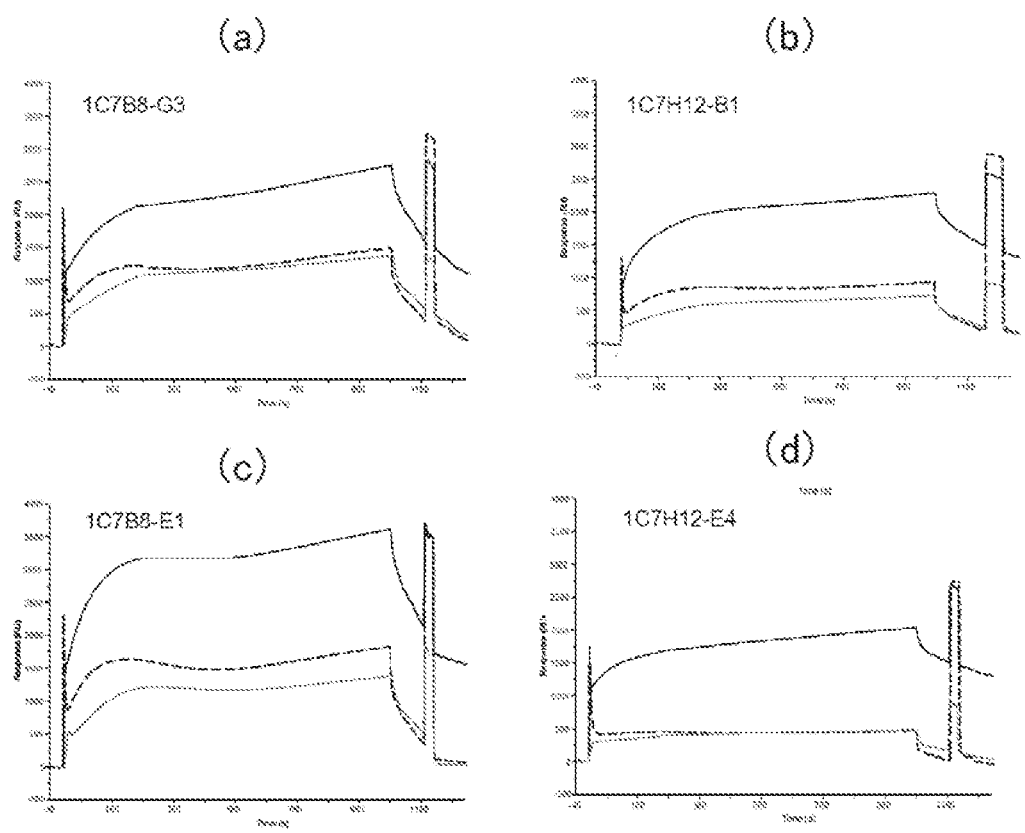
FIG. 3 is a figure showing the results of SPR.
Figure 4:
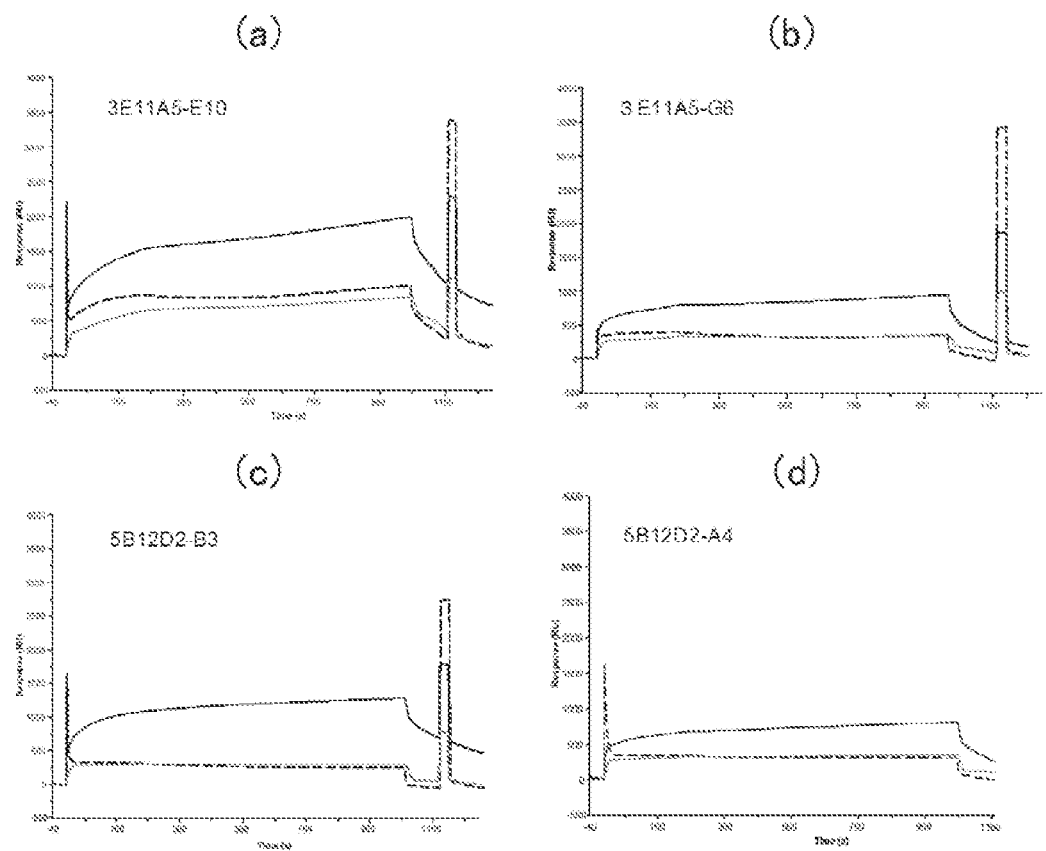
FIG. 4 is a figure showing the results of SPR.

The results of ELISA of these eight clones were shown in FIGS. 1 and 2 and the results of SPR were in FIGS. 3 and 4 (in FIGS. 3 and 4, solid line: KIR2DS1, dashed line: KIR2DL1, gray line: BSA). The results of ELISA are consistent with the results of SPR; and thus these eight clones have been shown not to bind to KIR2DL1, KIR2DS2, KIR2DL2, and KIR2DL3 and to specifically bind only to KIR2DS1.

It is to be noted that the hybridoma which produced 1C7B8-G3, 1C7H12-B1, 1C7B8-E1, and 1C7H12-E4 (1C7_KIR2DS1), the hybridoma which produced 3E11A5-E10 and 3E11A5-G6 (3E11A5_KIR2DS1), and the hybridoma which produced 5B12D2-B3 and 5B12D2-A4 (5B12D2_KIR2DS1) have been deposited with Incorporated Administrative Agency National Institute of Technology and Evaluation (NITE) Patent Microorganisms Depositary (NPMD) (2-5-8 Kazusakamatari, Kisarazu-shi, Chiba 292-0818, Japan) as of May 9, 2014 (date of deposition), thereafter transferred to International Deposit under the Budapest Treaty (the transfer request was received on Jul. 8, 2015), and given Accession No. NITE BP-01853, Accession No. NITE BP-01855, and Accession No. NITE BP-01854, respectively (the Receipt of a Deposit was issued on Jul. 29, 2015).

Example 3

VL and VH of eight clones of the monoclonal antibodies obtained in Example 2 were subjected to cloning; and the CDR sequence of VH and VL was determined.

RNA was extracted from the hybridoma (1C7_KIR2DS1, 3E11A5_KIR2DS1, and 5B12D2_KIR2DS1) by using TRIZOL (Invitrogen) and subjected to an RT reaction using BcaBEST RNA PCR Kit Ver.1.1 (Takara Bio Inc.) to thereby yield a PCR sample. PCR was carried out by using a primer mixture shown in Table 4 and Table 5. To be more specific, with regard to VL, the primer mixture of 26 kinds of Forward primers (RatVL-F01 to 26, SEQ ID NOs: 31 to 56) and five kinds of Reverse primers (RatVL-R01 to 05, SEQ ID NOs: 57 to 61) or three kinds thereof (RatCL-R01 to 03, SEQ ID NOs: 62 to 64) were used (Table 4). In addition, with regard to VH, the primer mixture of 24 kinds of Forward primers (RatVH-F01 to 24, SEQ ID NOs: 65 to 88) and four kinds of Reverse primers (RatVH-R01 to 04, SEQ ID NOs: 89 to 92) were used (Table 5). Conditions for a PCR reaction are as follows: (Ex Taq (Takara Bio Inc.) was used in PCR.)

| | |
|---|---|
| Template (1/10 dilution) | 1.0 µL |
| 10 × Ex Taq buffer | 5.0 µL |
| dNTP (2.5 mM each) | 4.0 µL |
| Forward primer mixture | 1.5 µL |
| Reverse primer mixture | 1.0 + 1.0 µL |
| Ex Taq | 0.25 µL |
| Water | 37.65 µL |
| Total | 50.0 µL |

PCR was carried out in conditions of 95° C. for 2 minutes, 95° C. for 30 seconds—45° C. for 30 seconds—68° C. for 1 minute×35 cycles, 68° C. for 1 minute, 4° C.×∞. Subsequently, TA cloning was carried out using pGEM-T Easy system I (Promega Corporation). An insert was confirmed by colony PCR; and then plasmid DNA was extracted by miniprep and subjected to sequencing.

TABLE 4

| | | | |
|---|---|---|---|
| VL forward | RatVL-F01 | racattgtshtgacycagtctc | SEQ ID NO: 31 |
| | RatVL-F02 | gaaactgtgatgacccagtc | SEQ ID NO: 32 |
| | RatVL-F03 | caggctgttgtgactcagg | SEQ ID NO: 33 |
| | RatVL-F04 | gamactrydstgacccagtc | SEQ ID NO: 34 |
| | RatVL-F05 | racrtccagwtracccagwct | SEQ ID NO: 35 |
| | RatVL-F06 | gacatccayatgacwcagwm | SEQ ID NO: 36 |
| | RatVL-F07 | gayatccrgrtgacwcagtc | SEQ ID NO: 37 |
| | RatVL-F08 | gacatvsrgatgacvmagtctc | SEQ ID NO: 38 |
| | RatVL-F09 | gacatytkgatgacymagtctc | SEQ ID NO: 39 |
| | RatVL-F10 | gacattkygatracccartmt | SEQ ID NO: 40 |
| | RatVL-F11 | gatattgtgatgachcarrs | SEQ ID NO: 41 |
| | RatVL-F12 | gatgttgtgwtgacacaaactc | SEQ ID NO: 42 |
| | RatVL-F13 | gatgttgttttggtgacaca | SEQ ID NO: 43 |
| | RatVL-F14 | gatgttgtgatgacccag | SEQ ID NO: 44 |
| | RatVL-F15 | gatgttrtgmtgrcccagac | SEQ ID NO: 45 |
| | RatVL-F16 | gamattgtgmtsayycagtctc | SEQ ID NO: 46 |
| | RatVL-F17 | gamattrtrctvacccagtct | SEQ ID NO: 47 |
| | RatVL-F18 | gawawtgtkctmmctcagtc | SEQ ID NO: 48 |
| | RatVL-F19 | gacgttgtctgactcagtc | SEQ ID NO: 49 |
| | RatVL-F20 | gayatcrtkhtractcagtctc | SEQ ID NO: 50 |
| | RatVL-F21 | cagcccgtgctgcatcag | SEQ ID NO: 51 |
| | RatVL-F22 | cagwtcacgctsacvcarcm | SEQ ID NO: 52 |
| | RatVL-F23 | cagkytgtscttactcagyc | SEQ ID NO: 53 |
| | RatVL-F24 | actggagaaacaacacagtc | SEQ ID NO: 54 |
| | RatVL-F25 | actgtggccttagagcagg | SEQ ID NO: 55 |
| | RatVL-F26 | agctatgagctgatccaacc | SEQ ID NO: 56 |
| VL Reverse | RatVL-R01 | acstttcarytccwgcytgg | SEQ ID NO: 57 |
| | RatVL-R02 | acgtttyatttccarctksgtc | SEQ ID NO: 58 |
| | RatVL-R03 | abstttgatctccagyttggtc | SEQ ID NO: 59 |
| | RatVL-R04 | taggacagtsagyktkgttccwc | SEQ ID NO: 60 |
| | RatVL-R05 | ccggctttcaggcag | SEQ ID NO: 61 |
| VL Reverse | RatCL-R01 | ctcattcctgttgaagctcttgacgacggg | SEQ ID NO: 62 |
| | RatCL-R02 | acactcagcacgggacaaactcttctccacagt | SEQ ID NO: 63 |
| | RatCL-R03 | acactctgcaggagacagactctttccacagt | SEQ ID NO: 64 |

TABLE 5

| | | | |
|---|---|---|---|
| VH forward | RatVH-F01 | aggtrcarctramrgagtcagg | SEQ ID NO: 65 |
| | RatVH-F02 | aggtgsakmtgaaggagwc | SEQ ID NO: 66 |
| | RatVH-F03 | argtgcagykgawggagtc | SEQ ID NO: 67 |
| | RatVH-F04 | aggthcagctgcascartct | SEQ ID NO: 68 |
| | RatVH-F05 | aggthcagctgtaccartct | SEQ ID NO: 69 |
| | RatVH-F06 | agatccagttggyacagtc | SEQ ID NO: 70 |
| | RatVH-F07 | aggcccagctgcagtctgg | SEQ ID NO: 71 |
| | RatVH-F08 | aggtccagytgcagcarts | SEQ ID NO: 72 |
| | RatVH-F09 | agattcagctgcarcagtg | SEQ ID NO: 73 |
| | RatVH-F010 | aaacagtccagctacagcagtc | SEQ ID NO: 74 |
| | RatVH-F011 | aagargtccwgctgcakcagtm | SEQ ID NO: 75 |
| | RatVH-F012 | aggttmmtctgmaasagtc | SEQ ID NO: 76 |
| | RatVH-F013 | argtyaasctrcwgcagtc | SEQ ID NO: 77 |
| | RatVH-F014 | aagaggtaaagctgcarcagtc | SEQ ID NO: 78 |
| | RatVH-F015 | aagargttcarctgcagcagtc | SEQ ID NO: 79 |
| | RatVH-F016 | aagaggtgcarmttcwggagwc | SEQ ID NO: 80 |
| | RatVH-F017 | aagaggtgcarmttttggagwc | SEQ ID NO: 81 |
| | RatVH-F018 | aagaggtgaaacttgtcgagtc | SEQ ID NO: 82 |
| | RatVH-F019 | aagvggtgcagctwgtkgagwc | SEQ ID NO: 83 |
| | RatVH-F020 | aagargtgcarytggtggartc | SEQ ID NO: 84 |
| | RatVH-F021 | aagaagtgaarctggwrgartctgg | SEQ ID NO: 85 |
| | RatVH-F022 | aagaagtgaarctgttrgartctgg | SEQ ID NO: 86 |
| | RatVH-F023 | aagmrgtacagctrgtkgagtc | SEQ ID NO: 87 |
| | RatVH-F024 | aagaggtgcagctgaaggaatc | SEQ ID NO: 88 |
| VH reverse | RatVH-R01 | kgaggasacggtgaccrkgg | SEQ ID NO: 89 |
| | RatVH-R02 | tgaggagactgtgagagtgg | SEQ ID NO: 90 |
| | RatVH-R03 | tgargagactrtgrycrtgac | SEQ ID NO: 91 |
| | RatVH-R04 | tgargagacagwgacyrrag | SEQ ID NO: 92 |

The results of CDR sequence analysis are shown in Table 6. All of the sequences of CDRs 1 to 3 of VL were shown to be identical. On the other hand, with regard to VH, the sequence of CDR2 was identical; but the sequence of CDRs 1 and 3 was varied among clones as shown in Table 6. The results of CDR sequence analysis revealed that 1C7B8-G3, 1C7H12-B1, 1C7B8-E1, and 1C7H12-E4 were likely to be the same clone; 3E11A5-E10 and 3E11A5-G6 were likely to be the same clone; and 5B12D2-B3 and 5B12D2-A4 were likely to be the same clone.

In addition, the isotype of each antibody was determined using RAT MONOCLONAL ANTIBODY ISOTYPING KIT (Cosmo Bio Co., Ltd.); and the result showed that 3E11A5-E10 and 3E11A5-G6 were IgG2a/κ and the others were IgG2b/κ.

TABLE 6

| | VL | | |
|---|---|---|---|
| | CDR1 | CDR2 | CDR3 |
| 1C7B8-G3 | KASQNVGSNVD | KASNRYT | MQSNTNPLT |
| 1C7H12-B1 | (SEQ ID NO: 1) | (SEQ ID NO: 2) | (SEQ ID NO: 3) |
| 1C7B8-E1 | | | |
| 1C7H12-E4 | | | |
| 3E11A5-E10 | | | |
| 3E11A5-G6 | | | |
| 5B12D2-B3 | | | |
| 5B12D2-A4 | | | |

| | VH | | |
|---|---|---|---|
| | CDR1 | CDR2 | CDR3 |
| 1C7B8-G3 | GFSLSTYSMGVS | ASIWWNGNT | TEIIRGRNYYVMDA |
| 1C7H12-B1 | (SEQ ID NO: 4) | YNNPSLKS | (SEQ ID NO: 7) |
| 1C7B8-E1 | | (SEQ ID NO: 6) | |
| 1C7H12-E4 | | | |
| 3E11A5-E10 | GFSLSTYGMGVS | | TLITITPFYYVMDA |
| 3E11A5-G6 | (SEQ ID NO: 5) | | (SEQ ID NO: 8) |
| 5B12D2-B3 | | | TLITIAAISHY-YVMDA |
| 5B12D2-A4 | | | (SEQ ID NO: 9) |

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

The present application is based on Japanese Patent Application No. 2014-176094 filed on Aug. 29, 2014 and includes the specifications, claims, drawings, and abstract thereof. The disclosure in the above Japanese Patent Application is incorporated in the present specification by reference in their entirety.

Sequence Listing

15F055-PCT_Sequence Listing

The invention claimed is:

1. A monoclonal antibody to KIR2DS1, or the fragment comprising an antigen-binding region thereof, that includes a VL and a VH, wherein:
the VL comprises the amino acid sequence of SEQ ID NO: 1 as CDR1, the amino acid sequence of SEQ ID NO: 2 as CDR2, and the amino acid sequence of SEQ ID NO: 3 as CDR3; and
the VH comprises the amino acid sequence of SEQ ID NO: 4 or SEQ ID NO: 5 as CDR1, the amino acid sequence of SEQ ID NO: 6 as CDR2, and the amino acid sequence of SEQ ID NO: 7, SEQ ID NO: 8, or SEQ ID NO: 9, as CDR3;
wherein said antibody or fragment comprising an antigen-binding region thereof binds to KIR2DS1 specifically, in distinction to KIR2DL1, KIR2DS2, KIR2DL2, and KIR2DL3.

2. The monoclonal antibody to KIR2DS1, or fragment comprising an antigen-binding region thereof, according to claim 1 wherein:
the VL comprises the amino acid sequence of SEQ ID NO: 1 as CDR1, the amino acid sequence of SEQ ID NO: 2 as CDR2, and the amino acid sequence of SEQ ID NO: 3 as CDR3; and wherein:
the VH comprises the amino acid sequence of SEQ ID NO: 4 as CDR1, the amino acid sequence of SEQ ID NO: 6 as CDR2, and the amino acid sequence of SEQ ID NO: 7 as CDR3;
the VH comprises the amino acid sequence of SEQ ID NO: 5 as CDR1, the amino acid sequence of SEQ ID NO: 6 as CDR2, and the amino acid sequence of SEQ ID NO: 8 as CDR3; or
the VH comprises the amino acid sequence of SEQ ID NO: 5 as CDR1, the amino acid sequence of SEQ ID NO: 6 as CDR2, and the amino acid sequence of SEQ ID NO: 9 as CDR3.

3. The monoclonal antibody or the fragment comprising an antigen-binding region thereof according to claim 1 wherein the monoclonal antibody is a chimeric antibody or a humanized antibody.

4. The monoclonal antibody or the fragment comprising an antigen-binding region thereof according to claim 1 that acts as an agonist for KIR2DS1.

5. The monoclonal antibody or the fragment comprising an antigen-binding region thereof according to claim 1 that acts as antagonist against KIR2DS1.

6. The monoclonal antibody or the fragment comprising an antigen-binding region thereof according to claim 1 that neither acts as an agonist for KIR2DS1 nor acts as an antagonist against KIR2DS1.

7. A monoclonal antibody to KIR2DS1 that is produced by at least one hybridoma selected from the group consisting of a hybridoma with Accession No. NITE BP-01853, a hybridoma with Accession No. NITE BP-01855, and a hybridoma with Accession No. NITE BP-01854 or a fragment comprising an antigen-binding region thereof.

8. A pharmaceutical composition comprising the monoclonal antibody or the fragment comprising an antigen-binding region thereof according to claim 1.

9. A nucleic acid comprising a base sequence encoding the monoclonal antibody or the fragment comprising an antigen-binding region thereof according to claim 1.

10. An expression vector comprising the nucleic acid according to claim 9.

11. A transformant comprising the nucleic acid according to claim 9 or the expression vector according to claim 10 and producing the monoclonal antibody or the fragment comprising an antigen-binding region thereof according to claim 1.

12. A cell producing the monoclonal antibody or the fragment comprising an antigen-binding region thereof according to claim 1.

13. The cell according to claim 12 that is at least one hybridoma selected from the group consisting of a hybridoma with Accession No. NITE BP-01853, a hybridoma with Accession No. NITE BP-01855, and a hybridoma with Accession No. NITE BP-01854.

14. A method of producing the monoclonal antibody or the fragment comprising an antigen-binding region thereof according to claim 1, the method comprising a step of culturing the transformant according to claim 11 to collect the antibody or the fragment comprising an antigen-binding region thereof from a culture.

* * * * *